US005602321A

United States Patent [19]

John

[11] Patent Number: 5,602,321
[45] Date of Patent: *Feb. 11, 1997

[54] TRANSGENIC COTTON PLANTS PRODUCING HETEROLOGOUS POLYHYDROXY(E) BUTYRATE BIOPLASTIC

[75] Inventor: Maliyakal John, Middleton, Wis.

[73] Assignee: Monsanto Company, St. Louis, Mo.

[*] Notice: The term of this patent shall not extend beyond the expiration date of Pat. No. 5,495,070.

[21] Appl. No.: 241,943

[22] Filed: May 12, 1994

Related U.S. Application Data

[63] Continuation of Ser. No. 980,521, Nov. 20, 1992, abandoned.

[51] Int. Cl.[6] .......................... C12N 15/29; C12N 15/82; C12N 5/04; A01H 5/00
[52] U.S. Cl. .................... 800/205; 800/250; 800/200; 800/255; 800/DIG. 27; 800/DIG. 63; 435/172.3; 435/252.3; 435/69.1; 435/419; 536/23.1; 536/23.2; 536/23.6; 536/24.1
[58] Field of Search ..................... 800/205, 250, 800/200, 255, DIG. 63, DIG. 27; 435/172.3, 69.1, 240.4, 252.3; 536/23.1, 23.2, 23.6, 24.1

[56] References Cited

U.S. PATENT DOCUMENTS 4,393,167  7/1983  Holmes et al. .................... 525/64

FOREIGN PATENT DOCUMENTS

| 0396289A2 | 11/1990 | European Pat. Off. . |
| 0440165A2 | 8/1991 | European Pat. Off. . |
| WO8800948 | 2/1988 | WIPO . |
| WO8900202 | 1/1989 | WIPO . |
| WO9100917 | 1/1991 | WIPO . |
| WO9118995 | 12/1991 | WIPO . |
| WO9302187 | 2/1993 | WIPO . |

OTHER PUBLICATIONS

Peoples et al. 1989. J. Biol. Chem. 264: 15293–7.
Pool. 1989. Science. 245:1187–9.
Peoples et al. 198. J. Biol. Chem. 264:15298–303.
Josefsson et al. 1987. J. Biol. Chem. 262:12196–201.
Firoozabady et al. 1987. Plant Mol. Biol. 10:105–16.
Poirier et al. Apr. 1992. Science 256:520–3.
Umbeck et al. 1989. Crop Science 29:196–201.
John et al. 1989. J. Cell. Biochem. (Suppl. 13D) :280.
Jefferson et al. 1986. PNAS USA 83:8447–51.
Peoples, et al., "Biosynthetic Thialase from *Zoogloea ramigera*, III. Isolation and Characterization of the Structural Gene," *Journal of Biological Chemistry*, pp. 97–102 (1986).
Peoples and Sinskey, "Poly–B–hydroxybutyrate Biosynthesis in *Alcaligenes eutrophus* H16, Characterization of the Genes Encoding B–Ketothiolase and Acetoacetyl–CoA Reductase," *Journal of Biological Chemistry*: 264[26] 15293–15297 (1989).
Peoples and Sinskey, "Poly–B–hydroxybutyrate (PHB) Biosynthesis in *Alcaligenes eutrophus* H16, Identification and Characterization of the PHB Polymerase Gene (phbC)," *Journal of Biological Chemistry*: 264 [26] 15298–15303 (1989).
Poirier et al., "Polyhydroxybutyrate, a Biodegradable Thermoplastic, Produced in Transgenic Plants," *Science*: 256:520–523 (1992).
Peoples and Sinskey, "Fine structural analysis of the *Zoogloea ramigera phbA–phbB* locus encoding B–ketothiolase and acetoacetyl–CoA reductase: nucleotide sequence of phbB," *Molecular Microbiology* 3[3]:349–357 (1989).
Pieper and Steinbuchel, "Identification, cloning and dsequence analysis of the poly (3–hydroxyalkanoic acid) synthase gene of the Gram–positive bacterium *Rhodococcus ruber*," *FEMS Microbiology Letters* 96:73–90 (1992).
Slade, Michelle, "Agracetus Patent Blankets Cotton," *BioWorld Today*, 3[211]: 1–3 (Oct. 28, 1992).
Pool, Robert, "In Search of the Plastic Potato," *Science*, 245:1187–1189 (1989).
Naj, Almal Kumar, "Plant's Genes Are Engineered to Yield Plastic," *The Wall Street Journal*, (Apr. 24, 1992).

*Primary Examiner*—David T. Fox
*Assistant Examiner*—Elizabeth C. Kemmerer
*Attorney, Agent, or Firm*—Quarles & Brady

[57] ABSTRACT

A fiber-producing plant comprising in its genome a heterologous genetic construct is disclosed. This genetic construct comprises a fiber-specific promoter and a coding sequence selected from the group consisting of sequences encoding bioplastic-producing genes. Preferably, the coding sequence is selected from the group consisting of ketothiolase, acetoacetyl-CoA reductase, and PHB synthase. Seeds of the plant containing this genetic construct and plant cells containing this construct are also disclosed.

12 Claims, 4 Drawing Sheets

E6-3B/Nos (A) Fragments

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: peptide ( i i i ) HYPOTHETICAL: YES ( x i ) SEQUENCE DESCRIPTION: SEQ ID NO:1:

ATGCTGGTAC CTTTTTTTTT TTTTTT    26

( 2 ) INFORMATION FOR SEQ ID NO:2:

( i ) SEQUENCE CHARACTERISTICS:
        ( A ) LENGTH: 1067 base pairs
        ( B ) TYPE: nucleic acid ( C ) STRANDEDNESS: double
            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
            ( A ) ORGANISM: Gossypium hirsutum
            ( B ) STRAIN: Coker 312
            ( D ) DEVELOPMENTAL STAGE: 15 day old fiber cells
            ( F ) TISSUE TYPE: fiber cells ( v i i ) IMMEDIATE SOURCE:
            ( A ) LIBRARY: CKFB15A1
            ( B ) CLONE: E6

( x i ) SEQUENCE DESCRIPTION: SEQ ID NO:2:

| | | | | | |
|---|---|---|---|---|---|
| ACACACACAA | GTAAAGCATT | AGCAACCATA | GCCATGGCTT | CCTCACCAAA | ACTCTTCTCT | 60 |
| ATGTCTATCC | TCTTCCTTTT | TGCCCTCTTC | TCCATGCAAA | TCCATGCTAG | AGAGTACTTC | 120 |
| AGCAAATTCC | CAAGAGTTAA | CATCAATGAG | AAAGAGACAA | CAACCAGAGA | GCAAAAGCAC | 180 |
| GAGACCTTCG | TTCCCCAGAC | CACCCAAAAG | CCAGAAGAAC | AAGAGCCAAG | GTTCATTCCT | 240 |
| GAAACCCAAA | ATGGTTATGG | CCTTTACGGC | CACGAGTCAG | GCTCAAGCCG | GCCCAGTTTC | 300 |
| ACCACCAAAG | AAACCTATGA | ACCCTATGTC | ACCCCTGTTA | GATTCCACCC | TGATGAGCCC | 360 |
| TATAACAGCA | TCCCCGAATC | CTCCAACAAT | AAAGACACTT | ACTACTACAA | CAAGAATGCC | 420 |
| TACGAGTCCA | CTAAGCAGCA | AAACTTGGGC | GAGGCCATTT | TCACCGAGAA | AGGATGGAGC | 480 |
| ACCAAGGAAA | ACCAGAACAA | CAACTACTAC | AACGGCAACA | ATGGTTACAA | CAATGGCGAG | 540 |
| AAGCAAGGCA | TGAGCGATAC | TAGGTACTTG | GAGAATGGAA | AGTACTACTA | TGACGTCAAG | 600 |
| AGTGAGAACA | ACTATTATCC | AAACCGGTTC | GACAACTCAA | GAGGAGTTGC | TTCGAGGAAC | 660 |
| GAGTTCAATG | AGAATCGTTA | CAACAACATG | GGAAGGTACC | ACCAGAACCA | AGAGGAGTTC | 720 |
| GAGGAAAGCG | AGGAAGAGTT | CGAACCCTGA | TCACCTGTCG | TACAGTATTT | CTACATTTGA | 780 |
| TGTGTGATTT | GTGAAGAACA | TCAAACAAAA | CAAGCACTGG | CTTAATATG | ATGATAAGTA | 840 |
| TTATGGTAAT | TAATTAATTG | GCAAAAACAA | CAATGAAGCT | AAAATTTTAT | TTATTGAGCC | 900 |
| TTGCGGTTAA | TTTCTTGTGA | TGATCTTTTT | TTTTATTTTC | TAATTATATA | TAGTTTCCTT | 960 |
| TGCTTTGAAA | TGCTAAAGGT | TTGAGAGAGT | TATGTTCTTT | TTCTCTTCCT | CTTTCTTTTT | 1020 |
| TAACTTTATC | AAACAATTTT | TGAATAAAAA | TGTGAGTATA | TTGTAAC | | 1067 |

( 2 ) INFORMATION FOR SEQ ID NO:3:

( i ) SEQUENCE CHARACTERISTICS:
            ( A ) LENGTH: 690 base pairs
            ( B ) TYPE: nucleic acid
            ( C ) STRANDEDNESS: double
            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
            ( A ) ORGANISM: Gossypium hirsutum
            ( B ) STRAIN: Coker 312
            ( D ) DEVELOPMENTAL STAGE: 15 day old fiber cells
            ( F ) TISSUE TYPE: fiber cells ( v i i ) IMMEDIATE SOURCE:
            ( A ) LIBRARY: CKFB15A1

(B) CLONE: B8

(x i) SEQUENCE DESCRIPTION: SEQ ID NO:3:

| | | | | | | |
|---|---|---|---|---|---|---|
| CACCAACGGA | CAATGCTTTC | TCCAGCCTTA | AATCGGGCAC | ATTGAATTCA | CTCACCGATG | 60 |
| AACAAAAAGT | GGAGCTGGTG | CAATTCCACA | TCGTCCCAAC | ATACCTCACC | TCGTCTCAGT | 120 |
| TCCAAACCAT | TAGCAATCCT | TTGAGAACCC | AAGCTGGTGA | TAGTGGCGAT | GGCAAGTTCC | 180 |
| CTCTCAATAT | CACCACTTCG | GGGAACTCCG | TGAATATAAC | AACAGGGTTG | ACAAACACCA | 240 |
| GTGTTTCCGG | CACTATTTAC | ACTGATGGTC | AGCTTGCTGT | TTATCAAATC | GATCAAGTTC | 300 |
| TTCAACCATT | GCAAATATTT | GCACCTAGGC | CTCCAGCTCC | AGCACCGGCA | CCGGCAAAGT | 360 |
| CGAAGAATAA | GAAGGCTACC | ACCGTTGCTG | ATAGCCCCGA | TGTTACCCCA | GCTGATAACT | 420 |
| CCAAAGCGGC | CACCTTGCAA | AATGTTGGTT | TGTTTGGAGT | TGCTGCTCTA | GTTATTGCAC | 480 |
| TTTCTTTGTG | ACCATGAAAA | TGGAGAAAAG | AAGAAGACAG | TGATTTTGAT | GGTGATCAAG | 540 |
| ATGGCGAGTG | TTTTTTATTT | TTTCAATAAT | TATCATTTAA | AAAATTTATG | TTCTGTATGA | 600 |
| ANGATTGAAT | TTTGAGTTTG | TCTTGTTGAT | TTCATTTATT | TTTGTTTTGA | AATTTCTTT | 660 |
| GTTATCTCTT | ATTTCTCAAT | TGTAATTGTG | | | | 690 |

(2) INFORMATION FOR SEQ ID NO:4:

(i) SEQUENCE CHARACTERISTICS:
        (A) LENGTH: 614 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Gossypium barbadense
        (B) STRAIN: Sea Island (v i i) IMMEDIATE SOURCE:
        (A) LIBRARY: EMBL-SI
        (B) CLONE: E6-3B (x i) SEQUENCE DESCRIPTION: SEQ ID NO:4:

| | | | | | | |
|---|---|---|---|---|---|---|
| AAATTATAGC | ATACCTCACG | ATGTGGGTGA | AGTAAAATTA | TTTAACAAAT | ATATTTTGAA | 60 |
| AAATTGATAA | AAATACTAAA | TGAGGTTTTG | GTTGAATAGT | AAGATATAAT | TATTACAAAT | 120 |
| TATAAATATG | TAGGTCAAA | ATCTATCATG | TGTATATTTG | TACTATTATT | CTATATAAAT | 180 |
| TGATAACCTT | ATAAAGTAT | CTAATTTAGT | TTATGGTTGA | TTGATCGATA | ATACCAAATT | 240 |
| TATTAAAAAT | TAATATTAGT | AAAGATATAT | AGTACAAAAC | TAAACATAAA | ATTTTATATG | 300 |
| TTAAGGAAAT | AGCGGAAAAA | ATATCATATT | TGTAGAACTG | TTTAGCAGTG | TGGGAGAATG | 360 |
| GGATCATTAC | AAGGAAAAAT | GAAATATATA | TCATTAATAC | CAAACATAAA | AGAAAGCGTC | 420 |
| TTTTGATAAA | GTTGTTATTG | GTGTAATGTG | AAGGGACCAC | AATCATCACC | ATTCACCACT | 480 |
| TGCTCCTAAT | TGAGTTGAAA | TCTTTTTACA | ACATAGAAAA | CTAGAAGATC | GCCCTTTCTT | 540 |
| GCTTCATATA | TATAGATTTT | GTATCATCGC | AATTTCACAT | CACACACACA | AGTAAAGCAT | 600 |
| TAGCAACCAT | AGCC | | | | | 614 |

(2) INFORMATION FOR SEQ ID NO:5:

(i) SEQUENCE CHARACTERISTICS:
        (A) LENGTH: 307 base pairs (B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Gossypium barbadense
(B) STRAIN: Sea Island (vii) IMMEDIATE SOURCE:
(A) LIBRARY: EMBL-SI
(B) CLONE: B8

(xi) SEQUENCE DESCRIPTION: SEQ ID NO:5:

```
TTTTTAATGG TGTTGGATGG TTATATTATA TCTCGATTAT ATATATTTTT TTTAAAAACC      60
GAAGTTGAAT GTCTAAATAG GAAGTAATTT TTTTAATATT ATTTTTTTAT AATATTTGAA     120
TCCGATATCT TATTTAAAAA CCATCGAAAT TTTTATTACT CAATCATTAC CGAAATAGAA     180
TCGGGCTAAA ATATTTCGAA AACTAAAAGT TTCACTTTTT ATATTGAAAA ACGAGGCTTT     240
GTGATTCTTA TAAATTTAAT TCATTGAAAT TTCATCAAGT AAAACAGAAG AATTATAAAT     300
CTCTAAA                                                               307
```

(2) INFORMATION FOR SEQ ID NO:6:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: oligonucleotide (iii) HYPOTHETICAL: YES (xi) SEQUENCE DESCRIPTION: SEQ ID NO:6:

```
GGACTAGCTC GAGATGACTG ACGTTGTCAT CG                                    32
```

(2) INFORMATION FOR SEQ ID NO:7:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: oligonucleotide (iii) HYPOTHETICAL: YES (xi) SEQUENCE DESCRIPTION: SEQ ID NO:7:

```
ACTGGAAGCT TTTATTTGCG CTCGACTGC                                        29
```

(2) INFORMATION FOR SEQ ID NO:8:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: oligonucleotide (iii) HYPOTHETICAL: YES (xi) SEQUENCE DESCRIPTION: SEQ ID NO:8:

ATTAAGGATC CATGACTCAG CGCATTGCG 29

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:9:

AAGTATCTAG ATCAGCCCAT ATGCAGGCC 29

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:10:

GGATTAGGAT CCGCAGGTCA GCCCATATGC 30

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:11:

GGATTAGGAT CCAAACGCCC GCCGCCTTG 29

( 2 ) INFORMATION FOR SEQ ID NO:12:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:12:

AACATGAATT CATGGCGACC GGCAAAGG 28

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:13:

AATTAGGATC CGCGAGATCT TGCCGCGTG 29

( 2 ) INFORMATION FOR SEQ ID NO:14:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:14:

CACGCGGCAA GATCTCGC 18

( 2 ) INFORMATION FOR SEQ ID NO:15:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:15:

TGTAAGGATC CTCATGCCTT GGCTTTGACG 30

( 2 ) INFORMATION FOR SEQ ID NO:16:

( i ) SEQUENCE CHARACTERISTICS:
                ( A ) LENGTH: 313 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

TCACCTGTCG TACAGTATTT CTACATTTGA TGTGTGATTT GTGAAGAACA TCAAACAAAA 60

CAAGCACTGG CTTTAATATG ATGATAAGTA TTATGGTAAT TAATTAATTG GCAAAAACAA 120

CAATGAAGCT AAAATTTTAT TTATTGAGCC TTGCGGTTAA TTTCTTGTGA TGATCTTTTT 180

TTTTATTTTC TAATTATATA TAGTTTCCTT TGCTTTGAAA TGCTAAAGGT TTGAGAGAGT 240

TATTGCTCTT TTTTTCTTCC TCTTTCTTTT TTAACTTTAT CATACAAATT TTGAATAAAA 300

ATGTGAGTAC ATT 313

( 2 ) INFORMATION FOR SEQ ID NO:17:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear (i i) MOLECULE TYPE: oligonucleotide (i i i) HYPOTHETICAL: YES (i v) ANTI-SENSE: NO (x i) SEQUENCE DESCRIPTION: SEQ ID NO:17:

ACCGAAATAG AATCGGGC                                                                 18

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: oligonucleotide (i i i) HYPOTHETICAL: YES (x i) SEQUENCE DESCRIPTION: SEQ ID NO:18:

GGAATTCGGA TCCTTTAGAG ATTTATAATT C                                                  31

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: oligonucleotide (i i i) HYPOTHETICAL: YES (x i) SEQUENCE DESCRIPTION: SEQ ID NO:19:

CCGTTAAGCT TTGATCACCT GTCGTACAG                                                     29

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: oligonucleotide (i i i) HYPOTHETICAL: YES (x i) SEQUENCE DESCRIPTION: SEQ ID NO:20:

TGACAGGATC CGTTACAATA TACTCACAT                                                     29

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: oligonucleotide (i i i) HYPOTHETICAL: YES (x i) SEQUENCE DESCRIPTION: SEQ ID NO:21:

GGAATCTGCA GTGATCACCT GTCGTACAG                                                     29

(2) INFORMATION FOR SEQ ID NO:22:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:22:

| TTGCTCGAGT | CGACGGATCT | AGTAACATAG | | | | 30 |

( 2 ) INFORMATION FOR SEQ ID NO:23:

( i ) SEQUENCE CHARACTERISTICS:
  ( A ) LENGTH: 1182 base pairs
  ( B ) TYPE: nucleic acid
  ( C ) STRANDEDNESS: double
  ( D ) TOPOLOGY: linear ( i i ) MOLECULE TYPE: genomic DNA ( i i i ) HYPOTHETICAL: NO ( x ) PUBLICATION INFORMATION:
  ( A ) AUTHORS: PEOPLES
    SINSKEY
  ( C ) JOURNAL: J. Biol. Chem.
  ( D ) VOLUME: 264
  ( F ) PAGES: 15293-15297
  ( G ) DATE: 1989

( x i ) SEQUENCE DESCRIPTION: SEQ ID NO:23:

| ATGACTGACG | TTGTCATCGT | ATCCGCCGCC | CGCACGCGG | TCGGCAAGTT | TGGCGGCTCG | 60 |
| CTGGCCAAGA | TCCCGGCACC | GGAACTGGGT | GCCGTGGTCA | TCAAGGCCGC | GCTGGAGCGC | 120 |
| GCCGGCGTCA | AGCCGGAGCA | GGTGAGCGAA | GTCATCATGG | CCAGGTGCT | GACCGCCGGT | 180 |
| TCGGGCCAGA | ACCCCGCACG | CCAGGCCGCG | ATCAAGGCCG | GCCTGCCGGC | GATGGTGCCG | 240 |
| GCCATGACCA | TCAACAAGGT | GTGCGGCTCG | GGCCTGAAGG | CCGTGATGCT | GGCCGCCAAC | 300 |
| GCGATCATGG | CGGGCGACGC | CGAGATCGTG | GTGGCCGGCG | GCCAGGAAAA | CATGAGCGCC | 360 |
| GCCCCGCACG | TGCTGCCGGG | CTCGCGCGAT | GGTTTCCGCA | TGGGCGATGC | CAAGCTGGTC | 420 |
| GACACCATGA | TCGTCGACGG | CCTGTGGGAC | GTGTACAACC | AGTACCACAT | GGGCATCACC | 480 |
| GCCGAGAACG | TGGCCAAGGA | ATACGGCATC | ACACGCGAGG | CGCAGGATGA | GTTCGCCGTC | 540 |
| GGCTCGCAGA | ACAAGGCCGA | AGCCGCGCAG | AAGGCCGGCA | AGTTTGACGA | AGAGATCGTC | 600 |
| CCGGTGCTGA | TCCCGCAGCG | CAAGGGCGAC | CCGGTGGCCT | TCAAGACCGA | CGAGTTCGTG | 660 |
| CGCCAGGGCG | CCACGCTGGA | CAGCATGTCC | GGCCTCAAGC | CCGCCTTCGA | CAAGGCCGGC | 720 |
| ACGGTGACCG | CGGCCAACGC | CTCGGGCCTG | AACGACGGCG | CCGCCGCGGT | GGTGGTGATG | 780 |
| TCGGCGGCCA | AGGCCAAGGA | ACTGGGCCTG | ACCCCGCTGG | CCACGATCAA | GAGCTATGCC | 840 |
| AACGCCGGTG | TCGATCCCAA | GGTGATGGGC | ATGGGCCCGG | TGCCGGCCTC | CAAGCGCGCC | 900 |
| CTGTCGCGCG | CCGAGTGGAC | CCCGCAAGAC | CTGGACCTGA | TGGAGATCAA | CGAGGCCTTT | 960 |
| GCCGCGCAGG | CGCTGGCGGT | GCACCAGCAG | ATGGGCTGGG | ACACCTCCAA | GGTCAATGTG | 1020 |
| AACGGCGGCG | CCATCGCCAT | CGGCCACCCG | ATCGGCGCGT | CGGGCTGCCG | TATCCTGGTG | 1080 |
| ACGCTGCTGC | ACGAGATGAA | GCGCCGTGAC | GCGAAGAAGG | GCCTGGCCTC | GCTGTGCATC | 1140 |
| GGCGGCGGCA | TGGGCGTGGC | GCTGGCAGTC | GAGCGCAAAT | AA | | 1182 |

( 2 ) INFORMATION FOR SEQ ID NO:24:

( i ) SEQUENCE CHARACTERISTICS:
   ( A ) LENGTH: 741 base pairs
   ( B ) TYPE: nucleic acid
   ( C ) STRANDEDNESS: double
   ( D ) TOPOLOGY: linear ( i i ) MOLECULE TYPE: genomic DNA ( i i i ) HYPOTHETICAL: NO ( x ) PUBLICATION INFORMATION:
   ( A ) AUTHORS: PEOPLES
            SINSKEY
   ( C ) JOURNAL: J. Biol. Chem.
   ( D ) VOLUME: 264
   ( F ) PAGES: 15293-15297
   ( G ) DATE: 1989

( x i ) SEQUENCE DESCRIPTION: SEQ ID NO:24:

| | | | | | | |
|---|---|---|---|---|---|---|
| ATGACTCAGC | GCATTGCGTA | TGTGACCGGC | GGCATGGGTG | GTATCGGAAC | CGCCATTTGC | 60 |
| CAGCGGCTGG | CCAAGGATGG | CTTTCGTGTG | GTGGCCGGTT | GCGGCCCCAA | CTCGCCGCGC | 120 |
| CGCGAAAAGT | GGCTGGAGCA | GCAGAAGGCC | CTGGGCTTCG | ATTTCATTGC | CTCGGAAGGC | 180 |
| AATGTGGCTG | ACTGGGACTC | GACCAAGACC | GCATTCGACA | AGGTCAAGTC | CGAGGTCGGC | 240 |
| GAGGTTGATG | TGCTGATCAA | CAACGCCGGT | ATCACCCGCG | ACGTGGTGTT | CCGCAAGATG | 300 |
| ACCCGCGCCG | ACTGGGATGC | GGTGATCGAC | ACCAACCTGA | CCTCGCTGTT | CAACGTCACC | 360 |
| AAGCAGGTGA | TCGACGGCAT | GGCCGACCGT | GGCTGGGGCC | GCATCGTCAA | CATCTCGTCG | 420 |
| GTGAACGGGC | AGAAGGGCCA | GTTCGGCCAG | ACCAACTACT | CCACCGCCAA | GGCCGGCCTG | 480 |
| CATGGCTTCA | CCATGGCACT | GGCGCAGGAA | GTGGCGACCA | AGGGCGTGAC | CGTCAACACG | 540 |
| GTCTCTCCGG | GCTATATCGC | CACCGACATG | GTCAAGGCGA | TCCGCCAGGA | CGTGCTCGAC | 600 |
| AAGATCGTCG | CGACGATCCC | GGTCAAGCGC | CTGGGCCTGC | CGGAAGAGAT | CGCCTCGATC | 660 |
| TGCGCCTGGT | TGTCGTCGGA | GGAGTCCGGT | TTCTCGACCG | GCGCCGACTT | CTCGCTCAAC | 720 |
| GGCGGCCTGC | ATATGGGCTG | A | | | | 741 |

( 2 ) INFORMATION FOR SEQ ID NO:25:

( i ) SEQUENCE CHARACTERISTICS:
      ( A ) LENGTH: 1770 base pairs
      ( B ) TYPE: nucleic acid
      ( C ) STRANDEDNESS: double
      ( D ) TOPOLOGY: linear ( i i ) MOLECULE TYPE: genomic DNA ( i i i ) HYPOTHETICAL: NO ( x ) PUBLICATION INFORMATION:
      ( A ) AUTHORS: PEOPLES
               SINSKEY
      ( C ) JOURNAL: J. Biol. Chem.
      ( D ) VOLUME: 264
      ( F ) PAGES: 15298-15303
      ( G ) DATE: 1989

( x i ) SEQUENCE DESCRIPTION: SEQ ID NO:25:

| | | | | | | |
|---|---|---|---|---|---|---|
| ATGGCGACCG | GCAAAGGCGC | GGCAGCTTCC | ACGCAGGAAG | GCAAGTCCCA | ACCATTCAAG | 60 |
| GTCACGCCGG | GGCCATTCGA | TCCAGCCACA | TGGCTGGAAT | GGTCCCGCCA | GTGGCAGGGC | 120 |
| ACTGAAGGCA | ACGGCACGC | GGCCGCGTCC | GGCATTCCGG | CCTGGATGC | GCTGGCAGGC | 180 |
| GTCAAGATCG | CGCCGGCGCA | GCTGGGTGAT | ATCCAGCAGC | GCTACATGAA | GGACTTCTCA | 240 |
| GCGCTGTGGC | AGGCCATGGC | CGAGGGCAAG | GCCGAGGCCA | CCGGTCCGCT | GCACGACCGG | 300 |

-continued

| | | | | | | |
|---|---|---|---|---|---|---|
| CGCTTCGCCG | GCGACGCATG | GCGCACCAAC | CTCCCATATC | GCTTCGCTGC | CGCGTTCTAC | 360 |
| CTGCTCAATG | CGCGCGCCTT | GACCGAGCTG | GCCGATGCCG | TCGAGGCCGA | TGCCAAGACC | 420 |
| CGCCAGCGCA | TCCGCTTCGC | GATCTCGCAA | TGGGTCGATG | CGATGTCGCC | CGCCAACTTC | 480 |
| CTTGCCACCA | ATCCCGAGGC | GCAGCGCCTG | CTGATCGAGT | CGGGCGGCGA | ATCGCTGCGT | 540 |
| GCCGGCGTGC | GCAACATGAT | GGAAGACCTG | ACACGCGGCA | AGATCTCGCA | GACCGACGAG | 600 |
| AGCGCGTTTG | AGGTCGGCCG | CAATGTCGCG | GTGACCGAAG | GCGCCGTGGT | CTTCGAGAAC | 660 |
| GAGTACTTCC | AGCTGTTGCA | GTACAAGCCG | CTGACCGACA | AGGTGCACGC | GCGCCCGCTG | 720 |
| CTGATGGTGC | CGCCGTGCAT | CAACAAGTAC | TACATCCTGG | ACCTGCAGCC | GGAGAGCTCG | 780 |
| CTGGTGCGCC | ATGTGGTGGA | GCAGGGACAT | ACGGTGTTTC | TGGTGTCGTG | GCGCAATCCG | 840 |
| GACGCCAGCA | TGGCCGGCAG | CACCTGGGAC | GACTACATCG | AGCACGCGGC | CATCCGCGCC | 900 |
| ATCGAAGTCG | CGCGCGACAT | CAGCGGCCAG | GACAAGATCA | ACGTGCTCGG | CTTCTGCGTG | 960 |
| GGCGGCACCA | TTGTCTCGAC | CGCGCTGGCG | GTGCTGGCCG | CGCGCGGCGA | GCACCCGGCC | 1020 |
| GCCAGCGTCA | CGCTGCTGAC | CACGCTGCTG | GACTTTGCCG | ACACGGGCAT | CCTCGACGTC | 1080 |
| TTTGTCGACG | AGGGCCATGT | GCAGTTGCGC | GAGGCCACGC | TGGGCGGCGG | CGCCGGCGCG | 1140 |
| CCGTGCGCGC | TGCTGCGCGG | CCTTGAGCTG | GCCAATACCT | TCTCGTTCTT | GCGCCCGAAC | 1200 |
| GACCTGGTGT | GGAACTACGT | GGTCGACAAC | TACCTGAAGG | GCAACACGCC | GGTGCCGTTC | 1260 |
| GACCTGCTGT | TCTGGAACGG | CGACGCCACC | AACCTGCCGG | GGCCGTGGTA | CTGCTGGTAC | 1320 |
| CTGCGCCACA | CCTACCTGCA | GAACGAGCTC | AAGGTACCGG | GCAAGCTGAC | CGTGTGCGGC | 1380 |
| GTGCCGGTGG | ACCTGGCCAG | CATCGACGTG | CCGACCTATA | TCTACGGCTC | GCGCGAAGAC | 1440 |
| CATATCGTGC | CGTGGACCGC | GGCCTATGCC | TCGACCGCGC | TGCTGGCGAA | CAAGCTGCGC | 1500 |
| TTCGTGCTGG | GTGCGTCGGG | CCATATCGCC | GGTGTGATCA | ACCCGCCGGC | CAAGAACAAG | 1560 |
| CGCAGCCACT | GGACTAACGA | TGCGCTGCCG | GAGTCGCCGC | AGCAATGGCT | GGCCGGCGCC | 1620 |
| ATCGAGCATC | ACGGCAGCTG | GTGGCCGGAC | TGGACCGCAT | GGCTGGCCGG | GCAGGCCGGC | 1680 |
| GCGAAACGCG | CCGCGCCCGC | CAACTATGGC | AATGCGCGCT | ATCGCGCAAT | CGAACCCGCG | 1740 |
| CCTGGGCGAT | ACGTCAAAGC | CAAGGCATGA | | | | 1770 |

TRANSGENIC COTTON PLANTS PRODUCING HETEROLOGOUS POLYHYDROXY(E) BUTYRATE BIOPLASTIC

This is a continuation of application Ser. No. 07/980,521 filed Nov. 20, 1992, now abandoned.

FIELD OF THE INVENTION

The present invention relates to the field of plant genetic engineering. In particular, the present invention relates to the creation of transgenic cotton plants containing a heterologous bioplastic.

BACKGROUND

Bioplastics

Bioplastics are biologically produced polymers with many of the properties of petroleum-derived plastics. Bioplastics are long carbon and oxygen chain polyesters, the basic chemical structure of which is:

The carbon to oxygen linkage is in the ester form. If the R group of the structure described above is an alkyl group, the structure is a polyhydroxyalkanoate (PHA). Most typically, R is a carbon chain of between 1 and 10 residues. R groups such as methyl, ethyl, propyl and butyl have been found in bioplastics.

Poly-beta-hydroxybutyric acid (PHB) is a form of PHA found as an intracellular storage compound in many species of bacteria. PHB was identified in *Bacillus megaterium* in 1925. (Lemoigne, M. *Ann Inst. Pasteur. Paris.*, 35: 144, 1925). Referring to the structure described above, if R is a methyl group, the compound is PHB. PHB is a biodegradable thermoplastic that serves as a carbon and energy source for the bacterium. Due to its high degree of crystallinity, PHB is hard and brittle. Holmes, et al., U.S. Pat. No. 4,393,167, discusses the use of PHB and PHB blends.

In many bacteria, PHB is synthesized via a three-step metabolic pathway in which the enzymes ketothiolase, NADP-dependent acetoactyl-CoA reductase, and PHB synthase (PHB polymerase) catalyze the conversion of acetyl CoA to PHB (Dawes and Senior, *Adv. Microb. Physiol.* 10: 135–266, 1973). The genes corresponding to these three enzymes have been cloned from *Alcaligenes eutrophus*. *E. coli* can be made to synthesize PHB after transformation with these genes (Slater et al., *J. Bacteriol.* 170: 4431–4436, 1988; Schubert et al., *J. Bacteriol.* 170: 5837–5847, 1988; Slater et al., Applied and *Environmental Microbiology*, 58: 1085–1094, 1992; Peoples and Sinskey, *J. Biol. Chem.*, 264: 15298–15303, 1989; Peoples and Sinskey, *J. Biol. Chem.*, 264: 15293–15297, 1989).

Bacterial genera producing bioplastics include Alcaligenes, Athiorhodium, Azotobacter, Bacillus, norcardia, Pseudomonas, Rhizobium, Spirillium, Zoogloea and Rhodococcus (Haywood et al. *Biotech. Lett.* 11: 471–476, 1989). Depending on the nutrient source, the bacteria incorporate hetropolymers of the D-isomer of the beta-hydroxyalkanoates. (Brandl et al., *Int. J. Bio. Macromol.*, 11: 49–55, 1989; Gross et al. *Macromolecule*, 22: 1106–1115, 1989). Thus, polymers containing 3-hydroxybutyrate units (3HB) 3-hydroxyvalerate units (3HV), 3-hydroxypropionate (3HP) units and 5-hydroxyvalerate (5HV) units have been produced under controlled conditions (European Patent Application 0 440 165 A2).

Due to its high degree of crystallinity, PHB is hard and brittle. On the other hand, copolymers of 3HB, 3HV, 3HP and 5HV may have a number of advantages in terms of moldability, thermal resistance to degradation, or impact resistance. By using specific carbon sources one may be able to incorporate unusual repeating units such as branched alkyl, bromo or phenyl groups in the molecule. (Lenz et al. in *Novel Biodegradable Microbial Polymers*. Ed: Dawes, E. A., vol. 186, pp. 23–25, 1990). Thus, it is very likely that microorganisms have the ability to incorporate various monomers other than D(−)-hydroxybutyrate into the polymer chain. Characteristics of PHB synthase enzyme determines the type of polymers synthesized. *A. eutrophus* can accumulate PHA containing $C_4$ and $C_5$ units while P. Oleovarans forms a PHA containing $C_8$ units. *Rodospirillum rubrum* produce PHA of $C_4$ to $C_7$ units. *P. putida, P. oleovarans, P. aeruginosa, P. flurescens* and *P. testeronii* were able to accumulate PHAs containing 3-hydroxyacid units in the range of $C_5$ to $C_{10}$. (Haywood et al., *Biotech. Lett.* 11: 471–476, 1989). In this regard, identification of different PHB synthase genes and their characterization in in vitro systems will permit the production of various novel polymers. Such substrates include $C_5$–$C_8$ linear 3-oxo thiolesters, oxoesters and methylene ketones (Peoples and Sinskey, WO 91/00917).

Bioplastics have properties that are advantageous for the plastics industry. Unlike synthetic plastics, bioplastics are biodegradable and could eventually become a renewable source of plastic that is not dependent on petroleum. PHAs can be flexible and moldable. Additionally, bioplastics are biocompatible. Because of these properties, bioplastics can advantageously be used in place of synthetic plastics.

Expression of bioplastics in plants such as corn and potatoes has been suggested. See WO 91 00917; Pool, *Science* 245: 1187–9, 1989. PHB has been expressed in recombinant *Arabidopsis thaliana* plants. Poirer et al., Science, 256: 520–523 (1992).

Genetic Engineering of Cotton

Although successful transformation and regeneration techniques have been demonstrated in model plants species such as tobacco (Barton et al., *Cell* 32: 1033–1043, 1983), similar results with cotton have only been achieved relatively recently. See, e.g. Umbeck et al. *Bio/Technology*, 5[3] 263–266 (1987); Firoozabady et al., *Plant Mol. Bio.* 10: 105–116 (1987); Finer and McMullen., *Plant Cell Rep.* 8: 586–589, 1990.

Cotton is one of the most important cash crops. Successful transformation and regeneration of genetically engineered cotton plants has the potential to be of significant value to this agriculturally important crop. One of the most important benefits potentially achievable from genetically engineering cotton plants is the alteration and modification of cotton fiber quantity and quality.

Cotton fiber (seed hair) is a differentiated single epidermal cell of the ovule. At maturity the fiber cell consists of a cell lumen, primary cell-wall and secondary cell-wall. The primary cell-wall is made up of pectic compounds, cellulose, and small amounts of protein. The secondary cell-wall consists of cellulose. At maturity, the cotton fiber contains 87% cellulose.

Cotton fiber development can be divided into initiation, primary cell-wall synthesis stage, secondary cell-wall deposition stage, and maturation phases. Many hundreds of genes are required for the differentiation and development of cotton fiber. Work on in vitro translated fiber proteins (Delmar et al., *J. Cell Sci.* 2: 33–50, 1985) and protein isolated from fiber (Graves and Stewart, *J. Exp. Bot.* 39: 59–69, 1988) clearly suggests differential gene expression during various developmental stages of the cell. Only a few of the genes involved in the biosynthesis of the large numbers of fiber-specific structural proteins, enzymes, polysaccharides, waxes or lignins have been identified (John and Crow, *Proc. Natl. Acad. Sci. USA*, 89: 5769–5773, 1992). Since these genes and their interactions with environment determine the quality of fiber, their identification and characterization is considered to be an important aspect of cotton crop improvement.

The quality of the cotton fiber is dependent on such factors as the extent of elongation and degree of secondary wall deposition. It is assumed that both a number of genes and environmental factors regulate the physical characteristics of the fiber such as length, strength and micronaire value. However, the genes responsible for cellulose synthesis and fiber development in cotton plants are heretofore entirely uncharacterized at a molecular level.

The most commercially useful plant fiber is derived from cotton (*Gossypium arboreum, Gossypium herbaceum, Gossypium barbadense* and *Gossypium hirsutum*). However, there are other fiber-producing plants with a potential commercial use. These plants include the silk cotton tree (Kapok, *Ceiba pentandra*), desert willow, creosote bush, winterfat, balsa, ramie, kenaf, hemp, roselle, jute, sisal abaca and flax.
Promoters Promoters are DNA elements that direct the transcription of RNA in cells. Together with other regulatory elements that specify tissue and temporal specificity of gene expression, promoters control the development of organisms. Thus, there has been a concerted effort in identifying and isolating promoters from a wide variety of plants and animals.

Many promoters function properly in heterologous systems. For example, promoters taken from plant genes such as rbcS, Cab, chalcone synthase and protease inhibitor from tobacco and Arabidopsis are functional in heterologous transgenic plants. (Reviewed by Benfey and Chua, *Science* 244: 174–181, 1989). Specific examples of transgenic plants include tissue-specific and developmentally regulated expression of soybean 7s seed storage protein gene in transgenic tobacco plants (Chen, et al. *EMBO J.* 7: 297–302, 1988.) and light-dependent organ-specific expression of *Arabidopsis thaliana* chlorophyll a/b binding protein gene promoter in transgenic tobacco (Ha and An, *Proc. Natl. Acad. Sci. USA* 85: 8017–8021, 1988). Similarly, anaerobically inducible maize sucrose synthase-1 promoter activity was demonstrated in transgenic tobacco (Yang and Russell, *Proc. Natl. Acad. Sci USA*, 87: 4144–4148, 1990). Tomato pollen promoters were found to direct tissue-specific and developmentally regulated gene expression in transgenic Arabidopsis and tobacco (Twell et al., *Development* 109: 705–713, 1990). Similarly, one cotton promoter has been shown to express a transgene in a fiber-specific manner (John and Crow, *Proc. Natl. Acad. Sci. USA*, 89: 5769–5773, 1992). Thus, some plant promoters can be utilized to express foreign proteins in specific tissues in a developmentally regulated fashion.

Many of the features of bioplastics could be advantageously combined with plant fiber. However, bioplastic-containing fiber-producing plants have neither been proposed nor created. What is needed in the art of molecular biology is a cotton plant containing heterologous bioplastic.

SUMMARY OF THE INVENTION

The present invention is a fiber-producing plant comprising in its genome a heterologous genetic construct. This construct comprises a fiber-specific promoter and a coding sequence selected from the group consisting of sequences encoding genes involved in bioplastic synthesis. The gene sequence encodes an enzyme capable of producing a bioplastic molecule from molecules present in the fiber-producing plant. The bioplastic molecule is a polyester. Preferably, the bioplastic molecule has the structure

wherein n>2 and

R is selected from the group consisting of alkyl, bromo and phenyl groups. Preferably R is a methyl, ethyl, propyl, butyl, bromo or phenyl group. Most preferably, R is a methyl group.

Preferably, the coding sequence is for ketothiolase, acetoactyl-CoA reductase, and PHB synthase and the plant is cotton. Also preferably, the construct contains a marker gene.

An object of the present invention is to create a fiber-producing plant with altered fiber.

Another object of the present invention is to create a cotton plant with bioplastic molecules combined with cotton fiber.

It is an advantage of the present invention that the bioplastic genes are expressed in a fiber-specific manner.

It is another advantage of the present invention that fiber with altered flexibility, strength, stiffness, absorbency, and thermal properties is created.

Other objects, advantages, and features of the present invention will become apparent upon examination of the specification and claims.

DESCRIPTION OF THE PREFERRED EMBODIMENT

Figure 1:
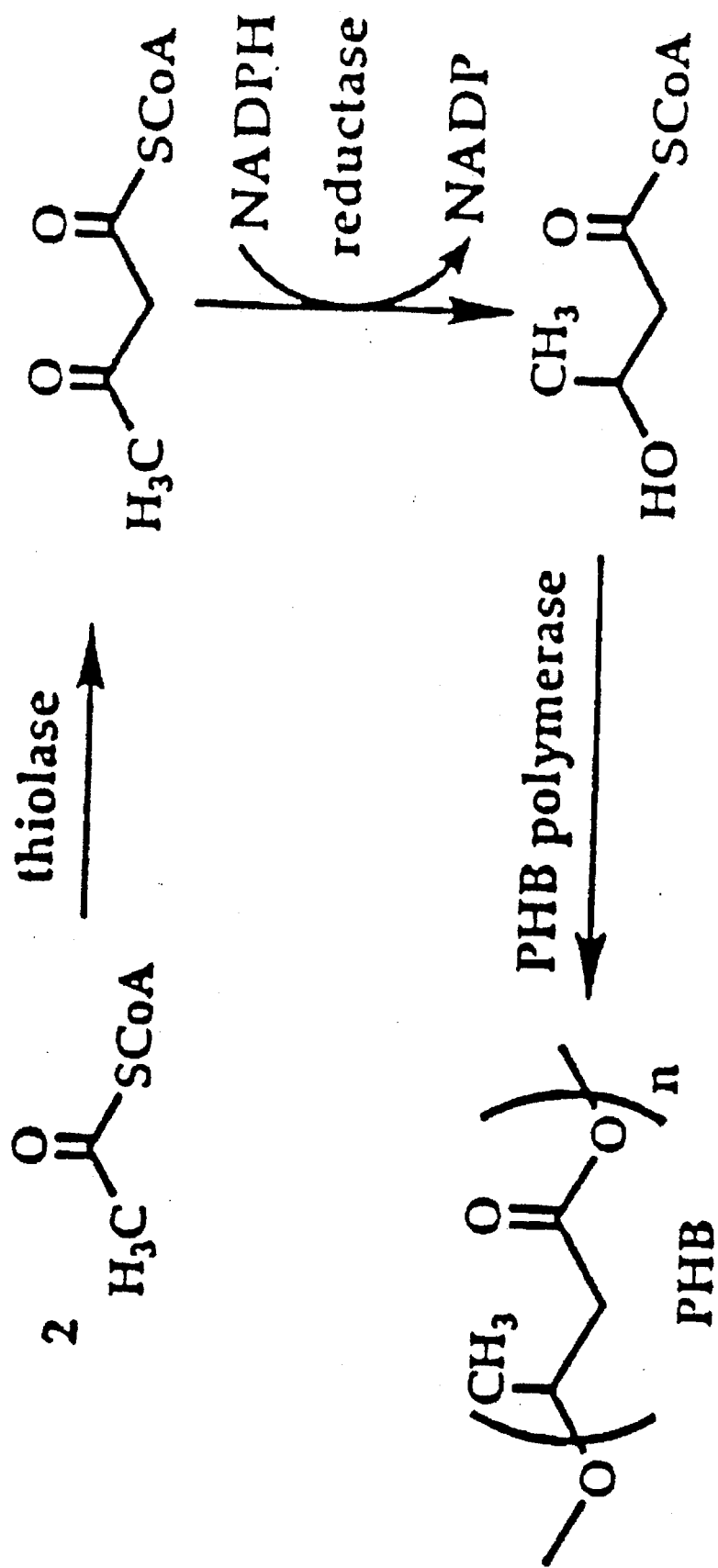
FIG. 1 is a diagram of PHB biosynthetic pathway.

The present invention is directed toward the creation of transgenic fiber-producing plants which have altered fiber characteristics. The altered fiber characteristics are caused by the transformation of plants with genes necessary to produce a bioplastic. In the Examples below, three genes are necessary to produce a specific bioplastic. However, the production of a different bioplastic might require a different number of genes. These genes are placed on individual plasmid vectors in the Examples. Alternatively, the genes could be placed on a single vector.

In the Examples below and in this discussion, we use cotton plants as an example of a fiber-producing plant. We refer to genes that encode enzymes capable of producing bioplastic as "bioplastic-producing genes." When we refer to a "bioplastic" or a "polyester," we mean to include all the various bioplastics discussed in this specification, such as PHA, PHB, 5HV, 3HB, 3HV, and 3HP. Preferably, the bioplastic is of the formula recited above, n>2 and R is an alkyl, bromo or phenyl group. By "alkyl" is meant both straight chain and branched alkyl groups and alkyl groups substituted with other groups, such as OH groups.

In order that the transgenes responsible for bioplastic production do not disrupt the morphological characteristics of the fiber-producing plant, the protein coding sequence for the gene is preferably placed downstream from a tissue-specific promoter which conditions expression of the gene preferentially in fiber cells.

To produce transgenic plants as described herein, three components are needed. The first component is a protein coding sequence or sequences which are sufficient to allow the production of bioplastics in fiber-producing plant cells. The second element is a promoter capable of causing expression of the transgenes in the fiber cells of the plant. Preferably, this promoter is fiber-specific. The third element is a transformation process by which a gene construct can be transferred into the germ line of a fiber-producing plant. All three of these elements will be discussed below.

Previous research with transgenic plants has demonstrated that transgenic plants are capable of passing on the inserted genes to their progeny by normal Mendelian inheritance. All such progeny plants which inherit the inserted genetic construct are also transgenic plants as the term is used here.

The specific traits of the altered cotton fiber are not yet characterized. However, the ability to insert bioplastic genes in fiber cells will likely cause morphological changes in the fiber and its development. For example, production of bioplastics in fiber cells may alter the flexibility, strength, stiffness, absorbency or thermal properties of the fiber. Bioplastics have many of the properties of synthetic plastics yet have the advantage that they are biodegradable. Therefore, cotton fiber containing bioplastics may have some properties of plastics, yet be completely biodegradable.

The water absorbency properties of bioplastic-containing fiber may be very different from those of natural cotton. For example, if the bioplastic-containing fiber absorbs less water, then the fiber can be used as a water barrier in many products such as diapers and personal care products. The texture of bioplastic-containing cotton is likely to be very different from those of natural ones. This property could be useful in applications such as carpets, furniture coverings, wall coverings, automobile seat covers or special textile applications.

Cotton has poor thermal adaptability and does not absorb or retain heat very well. However, plastics have this ability. Therefore, one advantage of a genetically engineered bioplastic-containing fiber may be that it absorbs and retains heat. This property will be useful in winter clothing.

In our Examples below, we have designed methods to produce PHB in fiber. However, other bioplastics or blends of PHB with other polymers may be useful due to the different properties of other bioplastics.

A. Fiber Specific Promoters.
1. In General

Promoters are DNA elements that initiate the transcription of a downstream protein coding sequence, a first step in the expression of genes. Promoters suitable for use in the present invention are capable of directing bioplastic biosynthesis in transgenic fiber-producing plants, preferably in a fiber-specific manner. Fiber-specific promoters will ensure that the bioplastics are synthesized only in fiber cells and, therefore, do not cause abnormal physiology in other tissues. Also, it is helpful that the promoters that direct the synthesis of bioplastic genes be developmentally regulated. It is helpful to have a battery of fiber-specific promoters of varying strengths in order to manipulate the concentrations of various bioplastic-producing enzymes.

We have isolated promoters from cotton that meet these criteria using the methods detailed below. Other suitable fiber-specific promoters may be isolated by this method or by using known cotton promoter sequences, such as SEQ ID NO:4 or 5, to probe a genomic library for homologous sequences.

In brief, fiber-specific cDNA clones are isolated from a fiber cDNA library through differential screening. Genomic clones are isolated by using the fiber-specific cDNA clones as probes to screen a cotton genomic library. Because it is known that promoter activity is found on the genomic DNA within the nucleotide sequence upstream from the start of RNA transcription, the cDNA and genomic clones are structurally characterized to enable us to isolate and identify these upstream genomic nucleotide sequences with potential promoter activity.

To determine whether the isolated sequence contains promoter activity, a chimeric gene construct containing the marker gene *E. coli* beta-glucuronidase (GUS) and a putative fiber promoter is introduced into cotton hypocotyl tissue. Detection of GUS activity by histochemical staining demonstrates that the promoter is active. The sequence of two exemplary fiber-specific promoters, E6-3B and B8, are presented below at SEQ ID NOs: 4 and 5 to make such a promoter generally available.

2. RNA Isolation From Fiber

The first step in the isolation of fiber-specific promoters is to isolate RNA from cotton fiber cells (John, *Nucl. Acid. Res.*, 20: 2381, 1992). We chose to isolate RNA from specific developmental stages of cotton fiber because we wanted a selection of fiber-specific promoters capable of regulation at different developmental stages. Nevertheless, if one wishes to obtain fiber-specific RNAs, RNA may be isolated from fiber cells at any stage of fiber development.

Ten-, fifteen- and twenty-three-day-old fiber cells from Coker 312 plants are collected and quick-frozen in liquid nitrogen. The 10-day fiber cells were selected to contain genes active during the primary cell-wall stage of cell development. In the 15-day cells, both primary cell-wall and secondary cell-wall synthesis systems are active. The 23-day-old fiber cells were selected to contain genes principally active during secondary wall synthesis.

The frozen fiber cells are powdered in a mortar in liquid nitrogen and homogenized for 1.5 minutes using a polytron in a homogenization buffer at full speed. The homogenization buffer is added at a ratio of 1:2 of tissue (weight) to buffer (volume). Homogenization buffer is: 5M guanidine isothiocyanate, 0.2M Tris-acetate (pH 8.5), 0.7% Beta-mercaptoethanol, 1% polyvinyl pyrrolidone (PVP, MW 40 Kd), and 0.62% sodium lauryl sarcosine. Beta-mercaptoethanol and PVP are added just before use.

The homogenate is filtered through Mira cloth and layered over a 1.5 ml pad of 5.7M cesium chloride as described by Chirgwin, J. M. et al. *Biochemistry*, 18: 5294–5299 (1979). The homogenate is then centrifuged for 18 hours at 36,000 rpm in a SW 50.1 rotor at 20° C. After centrifugation, the RNA is collected as described by Chirgwin, et al., (supra). The RNA is then further purified by phenol:chloroform extractions and precipitations in the presence of ammonium acetate, as described for DNA by Crouse, J. and Amorese D., *Focus*, 9[2]: 3–5 (1987).

Poly (A)$^+$ RNA was obtained by oligo-(dT) chromatography as described by Maniatis, et al., in *Molecular Cloning: A Laboratory Manual*, Cold Spring Harbor Laboratory, Cold Spring Harbor, N.Y., (1982).

3. Library Construction and cDNA Clone Identification

It is necessary to screen the isolated fiber RNA to determine which RNA sequences are fiber-specific. By the term "fiber-specific" we mean a sequence that is present either only in fiber cells or in a much higher abundance in fiber cells than in other plant cells. A standard technique used to identify tissue-specific sequences is to create cDNA clones from the RNA molecules isolated from a particular tissue and then to challenge the individual cDNA clones with radioactive cDNA created from RNA isolated from other tissues. cDNA clones that hybridize to fiber cDNA, but not cDNA derived from RNA from other plant tissues, contain a cDNA made from an mRNA that is fiber-specific. These mRNAs will likely be under the control of a fiber-specific promoter.

Complementary DNA libraries may be prepared by any standard technique. We chose to prepare separate cDNA libraries from the mRNAs from 10-day, 15-day and 23-day-old fiber cells according to the protocol developed by D'Alessio et al., *Focus*, 9[1]: 1–4 (1987) with the following exceptions: The first strand of cDNA is synthesized with a primer of the sequence set forth in SEQ ID NO: 1 below. For the 10-day-old fiber cell mRNAs, an oligo-(dT) primer is used instead. The second strand synthesis is carried out as described by D'Alessio et al., supra, for homopolymer tailing. Poly-(dC) tails are added to the double-stranded cDNA, which is annealed to poly-(dG)-tailed pBR322 plasmid vector (Bethesda Research Laboratories). *E. coli* RR1 strain is transformed with the recombinant plasmids as described by Hanahan in *DNA Cloning-A Practical Approach*, Vol. 1 (1985) p. 109–135. The transformed cells were selected on antibiotic tetracycline (12 mg/liter) containing agar plates.

The specific bacteria that harbored plasmids containing fiber-specific cDNAs are identified by differential screening. The clones in the library are transferred to nitrocellulose filters and duplicate filters were made according to Hanahan and Meselson, *Gene*, 10: 63–67 (1980). We screened about 25,000 clones from the 15-day and 23-day libraries using the following procedure: Radioactive probes are prepared from poly(A)$^+$ RNA of 15-day-old and 23-day-old fiber producing cells and from poly(A)$^+$ RNA of 0-day ovule, leaf, root and flower cells. The radioactive probes are prepared as described in Maniatis (supra) from $^{32}$P-dCTP and reverse transcriptase. The radioactive probes are exposed to the filters containing the clones. Prewashing, prehybridizations, hybridizations and washings of the filters are performed as described in detail in John et al., *Proc. Natl. Acad. Sci. USA*, 81: 5628–5632 (1984).

The autographic signals from duplicate filters hybridized with $^{32}$P-labelled cDNAs from the different tissues are compared and the clones which hybridized to cDNAs from fiber-producing cells, but not to cDNAs from other tissues, are identified and isolated. The identified clones are then subjected to three more cycles of differential screening as described above. This repetitive screening eliminated clones which hybridized to cDNAs from non-fiber-producing cells.

Alternatively, another method of screening a cDNA library for fiber-specific cDNA clones is by subtractive hybridization. In general, fiber cDNA is challenged with excess RNA from different tissues. Fiber cDNA that does not hybridize to the RNA preparations remains single-stranded. These non-hybridizing cDNA sequences are more likely to be fiber-specific. This procedure has been described by Duguid, et al., *Proc. Natl. Acad. Sci. USA*, 85 pp. 5738–5742 (1988).

We screened the cDNA library from the 10-day old cells using a subtractive hybridization procedure. In our procedure we first hybridize the $^{32}$P-labelled cDNA from fiber to excess biotinylated mRNA isolated from leaf tissue. The hybridized cDNA-biotinylated mRNA hybrids are reacted with streptavidin, which is a protein with a high affinity for biotin, and the biotinylated mRNAs are separated from unhybridized cDNA by extraction with avidin in phenol:chloroform. The streptavidin and biotinylated mRNA were partitioned into the organic phase while the single-stranded cDNA remained in the aqueous phase.

Subtractive hybridization screening of 4788 clones of the 10 day fiber cell cDNA library with leaf cell cDNAs resulted in the identification of 800 clones not present in the leaf cells. These clones were then screened with cDNAs generated from ovule, flower and root mRNAs. 79 putatively fiber-specific clones were obtained from this screening.

After obtaining fiber-specific clones, it is useful to examine RNA populations of the different tissues to determine whether the RNA encoded by the selected cDNA clone is within the population. This procedure is a double-check that the RNA is fiber-specific. The standard molecular biological method for examining a population of RNA for the presence of a particular sequence is a northern blot. For this analysis, poly(A)$^+$ RNA from different tissues is denatured in the presence of formaldehyde and size-fractionated by electrophoresis on 1.5% agar/formaldehyde gels. (John et al., supra). The RNAs are blotted onto nitrocellulose and probed with $^{32}$P-labelled inserts of each individual clone. The clones that hybridized to only RNAs from fiber-producing cells are selected. All manipulations on plasmid DNAs such as isolation, purification on cesium chloride gradients, restriction digestion, insert purifications by gel electrophoresis and electroelutions, and $^{32}$P-labelling by nick translations are standard techniques (e.g., see Maniatis et al., supra. and John et al., supra).

Several cDNA clones may correspond to the same RNA sequence. The number of unique RNA messages represented among the selected cDNA clones may be determined by cross-hybridizing the cDNA clones. Clones that hybridize to each other are generated either from the same RNA sequence or from a related RNA sequence. We detected cross-hybridizing clones by a polymerase chain reaction (PCR) procedure (Saiki et al., *Science*, 239 pp. 487–491 (1988)), Southern blotting and hybridization. The PCR reaction is carried out by first mixing 10 μl of bacterial culture of the cDNA clone with 90 μl of distilled water. Twenty μl of that mixture is added to a PCR reaction buffer of 50 mM KCl, 10 mM Tris-HCl pH 8.0, 2.5 mM MgCl$_2$, 0.01% gelatin, 200 μM each of dATP, dCTP, dTTP and dGTP, 12.5 picomolar each of sense and antisense primers for pBR322, and 0.5 units of Taq polymerase. The final reaction volume is 52 μl. The PCR reactions are carried out under standard conditions in a Perkin-Elmer-Cetus thermocycler.

The amplified DNA from the PCR reactions is separated by agarose gel electrophoresis and blotted onto nitrocellulose as in Southern, *J. Mol. Biol.* 98: 503–517 (1975). One or more DNA inserts of the bacterial clones from the same group are amplified by the same procedure and the products also separated on agarose gel. The amplified insert DNAs are then excised from the gel and purified by electroelution. The purified DNAs, labelled with $^{32}$P by nick translation, are hybridized with the Southern blot and the cross-hybridizing clones identified.

After northern hybridization and tests for cross-reactivity, we had approximately 20 putative fiber-specific clones. This number represents cDNAs from all three fiber cDNA libraries.

Although we characterized all the fiber-specific cDNAs and obtained genomic clones corresponding to these cDNAs, only two cDNA clones will be discussed further. These clones are E6 and B8. These cDNA clones and their corresponding genomic clones will serve as examples of the isolation and use of fiber-specific promoters.

a. CKFB15A1-E6 cDNA clone (E6 cDNA)

This cDNA clone for a fiber gene has an insert of 983 base pairs which hybridizes to 1.0 and 1.1 kb RNAs. The RNA is expressed in fiber and not in root. Flower, leaf and ovule RNAs show weak hybridization.

The E6 RNA was found to be developmentally regulated. Its steady-state concentration increases immediately after anthesis. Our quantification of E6 transcript in fiber using in vitro synthesized E6 RNA as a control shows that 20 ug of RNA from 20-day-old fiber contains about 3.5 ng of E6 RNA. Thus, E6 RNA is an abundant fiber RNA.

Hybrid selection translation experiments showed that E6 codes for two polypeptides of 26 and 30 kDa. The E6 cDNA clone cross-hybridizes with Pima and Naked seed cotton fiber cell RNAs. The clone also cross-hybridizes with a number of plants belonging to Gossypium species. Thus, DNAs from Pima and Sea Island (*G. barbadense*) PD3 and DP50 (*G. hirsutum*) and plants belonging to *G. longicalyx* and *G. somalense* all showed hybridization. In addition, plants belonging to another species of family Malvaceae, the Hibiscus, are also found to have conserved the E6 gene. DNAs of *H. sabdariffa* L. cv., Rosselle, Kapok (*Ceiba pentandra*) belonging to family Bombacaceae, and Hemp (*Cannabis sativa*) belonging to family Moraceae also showed hybridization to E6 gene. We confirmed that E6 or a homologous gene is present in *Gossypium darwinii, Gossypium herbaceum* L. cv. Jayadhar and Tzuyung, *Gossypium anomalum, G. australe, G. nelsonii, G. arboreim* L., cv., Nanking and Liaochung, *G. thurberi, G. davidsonii, G. raimondii, G. stocksii, G. somalense, G. longicalyx*, and *F. bickii*. Thus, the E6 sequence is conserved in most of the plants belonging to family Malvaceae and also found in two other families Bombacaceae and Moraceae. Many of these plants produce seed hair or bast fiber. Interestingly, we did not detect E6 hybridization in the DNAs of soybean, corn, tobacco or the cellulose-producing bacterium Acetobacter (*A. xylinum*). These studies imply that E6 gene may have functions in the formation of seed hair or bast fiber cells (John and Crow, supra).

The complete nucleotide sequence of E6 insert is presented as SEQ ID NO: 2. This sequence contains a long open reading frame extending from position 1 to position 748. On this same open reading frame, start codons appear at positions 34, 61 and 94. If the first codon is the initiation site for the protein, the 714 nucleotide reading frame would yield a 238 amino acid protein. E6 cDNA clone was deposited with ATCC at Accession Number 67809.

SEQ ID NO: 2 also contains an additional 84 residues and a stretch of poly(A) that originate from clone PCKFB15-B3. This clone is identical to pCKFB15A1-E6 except for the presence of additional residues at the 3' end.

b. CKFB15A1-B8 cDNA clone (B8 cDNA)

B8 RNA is 1100 bases long and is developmentally regulated. It is not expressed in leaf, root, ovule or flower. B8 cross-hybridizes to Pima, PD3 and Sea Island genomic DNAs and is encoded by one or two genes. The B8 cDNA clone has an insert of 690 bp, the sequence of which is presented at SEQ ID NO: 3 below. It has been deposited with ATCC at Accession Number 67807.

4. Preparation of Genomic DNA and Creation of Genomic Clones.

To isolate a promoter sequence, one must isolate the DNA sequence upstream from the site of RNA transcript initiation. We accomplished this by probing a library of cotton genomic clones with the fiber-specific cDNA clones. The description below describes a genomic library created from Sea Island cotton, but other cotton varieties would be suitable. We have also probed Coker 312 (another cotton variety) and Kapok (a related fiber-producing plant) libraries with our clones. We believe that fiber-specific promoters isolated from different cotton varieties are effective in other cotton varieties.

Genomic DNA from Sea Island cotton is prepared according to the methods of E. Richards described in *Current Protocols in Molecular Biology*, (Eds. Ausbel, F. M. et al.) Wiley, (1987) pp. 2.3.1–2.3.3, with the following modification: the frozen plant material was homogenized in extraction buffer containing 1% polyvinyl pyrrolidone. The purified genomic DNA is digested with restriction endonucleases and transferred to nitrocellulose filters by the Southern blotting technique. Southern, E. M., *J. Mol. Biol.*, 98: 503–517 (1975).

The filters are then probed with nick-translated inserts of the fiber-specific cDNA clones. The hybridization and blot washing conditions are described in John et al. (supra). Upon such a hybridization, we found that our fiber-specific cDNAs were represented in the cotton genome.

Sea Island cotton genomic libraries are prepared by ligation of the digested cotton DNA into a vector. We chose to have our cotton genomic library constructed by Clonetech, Inc., of California, in EMBL-3 vectors. When the fragments were initially cloned, a Sal I site was added to the fragment by the cloning vector. The designation "Sal I (Mbo I)" indicates that a naturally occurring Mbo I site exists adjacent to the artificial Sal I site. (The genomic fragments were originally created by a partial Mbo I digest.) Genomic inserts of about 10–15 kb were present in the EMBL3 phage library. The phage libraries are plated on *E. coli*. We chose to plate our phage library on *E. coli* NM 538 as described in *Current Protocols in Molecular Biology*, (supra, p. 6.0.1–6.8.5).

The phage library was screened with radioactive fiber-specific cDNA inserts. A number of phage that hybridized to B8 and E6 cDNA clones were identified. Genomic clones that we chose to examine further are described below. The nomenclature for the genomic clones is as follows: EMBL= Lambda vector; SI=Sea Island; E6=cDNA insert that hybridizes to genomic clone; the last number corresponds to different genomic clones from a given library. We obtained many different genomic clones corresponding to our fiber-specific cDNA clones. From these genomic clones, we isolated regions with promoter activity. SEQ ID NOS: 4 and 5 give sequence information for the E6-3B and B8 fiber-specific promoters.

For some of these clones, we have identified cross-hybridizing genomic clones from other cotton species. For example, we have two different genomic clones from the Sea Island cotton library that hybridize to E6 cDNA, as well as two genomic clones from the Coker 312 cotton library and one genomic clone from a Kapok library.

As an example of the isolation of fiber-specific promoters, below we give more detail concerning the isolation of two fiber-specific promoters-the B8 and E6 gene promoters. One wishing to practice the present invention could isolate fiber-specific cotton promoters from a cotton genomic library by either going through a differential screening and obtaining a fiber-specific cDNA to use as a probe, as we have described, or using sequences corresponding to those described here as probes to isolate corresponding promoters from the cotton genome.

5. Characterization of Fiber-Specific Promoters.

(a) In General

Once a genomic clone has been isolated, one must identify the DNA fragments that contain promoter activity within the large genomic insert. Comparison of the genomic clone with the corresponding cDNA clone will demonstrate which part of the genomic insert contains the upstream sequence. This comparison may be done through restriction mapping of both clones or hybridization of the cDNA clone to different restriction fragments of the genomic insert. Once a fragment with promoter activity has been identified, this fragment may be subcloned into a more convenient vector system.

(b) E6 Gene Promoters

We have identified two independent genomic clones, pEMBLSIE6-2 and pEMBLSIE6-3, that hybridize to E6 cDNA. Both phages contain 15 kb inserts. In this discussion, we will focus on pEMBLSIE6-3.

Figure 2:
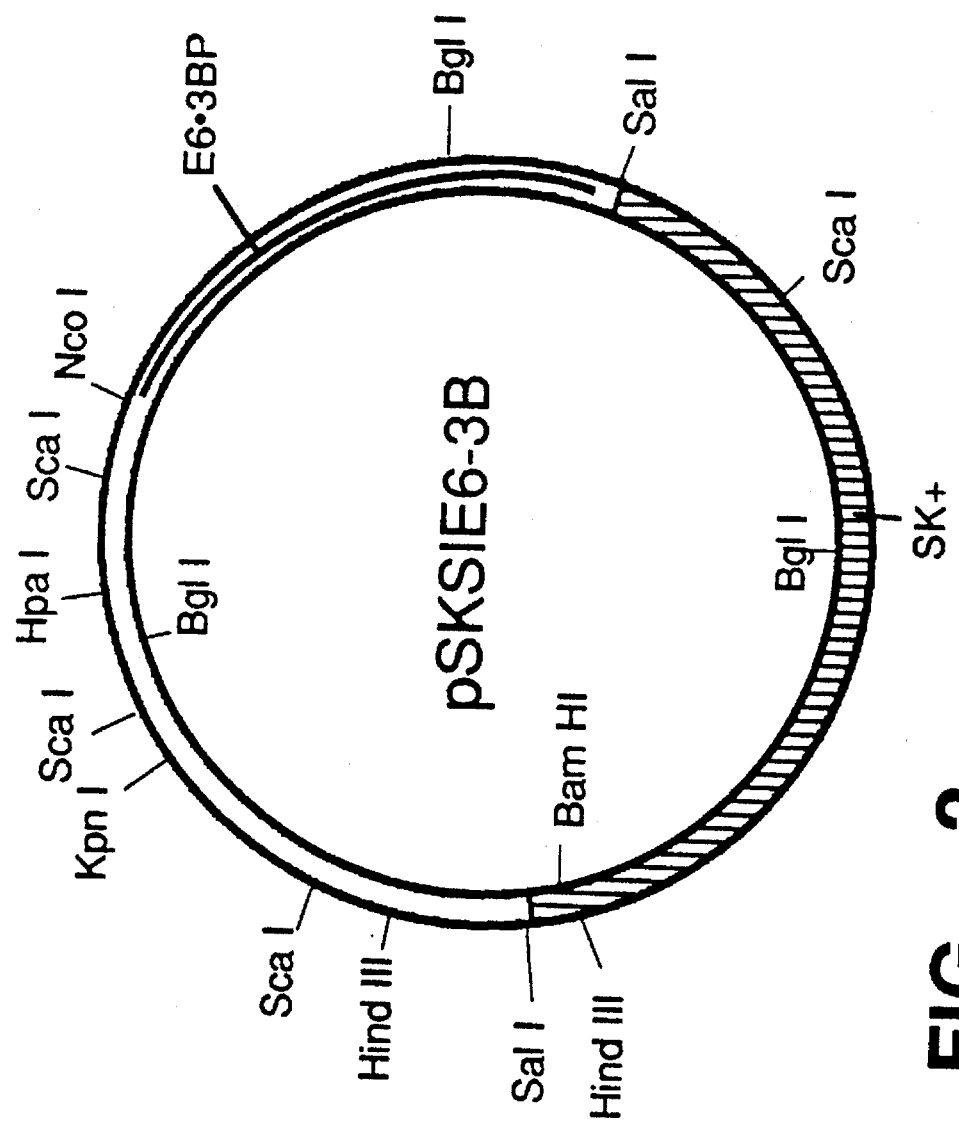
FIG. 2 is a diagram of pSKSIE6-3B.

One of the E6 genes, pEMBLSIE6-3, was subcloned into Bluescript Sk$^+$ vector as follows: A 5.0 kb Sal I fragment that hybridized to E6 cDNA was ligated into the Sal I site of Bluescript resulting in pSKSIE6-3B. FIG. 2 is a diagram of this construction. An Nco I/Sal I fragment (2.7 kb) contains the promoter of E6-3B gene. SEQ ID NO: 4 is the sequence of the 5' end of E6-3B gene. Comparison of the nucleotide sequences of E6-2A and E6-3B promoter regions (about 600 bp) shows no differences. However, it is clear that there are restriction polymorphisms between these genes further upstream. Furthermore, we have also identified sequence differences in the 3' ends of these genes. E6-2A and E6-3B promoters also show differences in their ability to express GUS gene in transient assays. E6-3B promoter is 3-fold stronger than E6-2A promoter.

(c) B8 Gene Promoter

EMBLSI-B8 was isolated as hybridizing to the B8 cDNA clone. A 9.5 kb Sal I/Bam HI fragment from the genomic clone was inserted into the SK vector to form pSKSIB8-HI. A 2.2 kb Bam HI/Bst BI fragment from the clone was assayed for promoter activity. SEQ ID NO: 5 is the partial sequence of this promoter fragment.

(d) Determination of E6 and B8 Promoter Activity

Once one has obtained a fragment of DNA with a putative promoter function, it is necessary to determine whether the sequence is capable of controlling transcription. This may be accomplished by ligating the putative promoter into a plasmid containing a marker gene, but no promoter, and assaying for the expression of the marker gene. We constructed such a system, along with the appropriate controls, to assay the function of our fiber-specific promoters.

Figure 3:
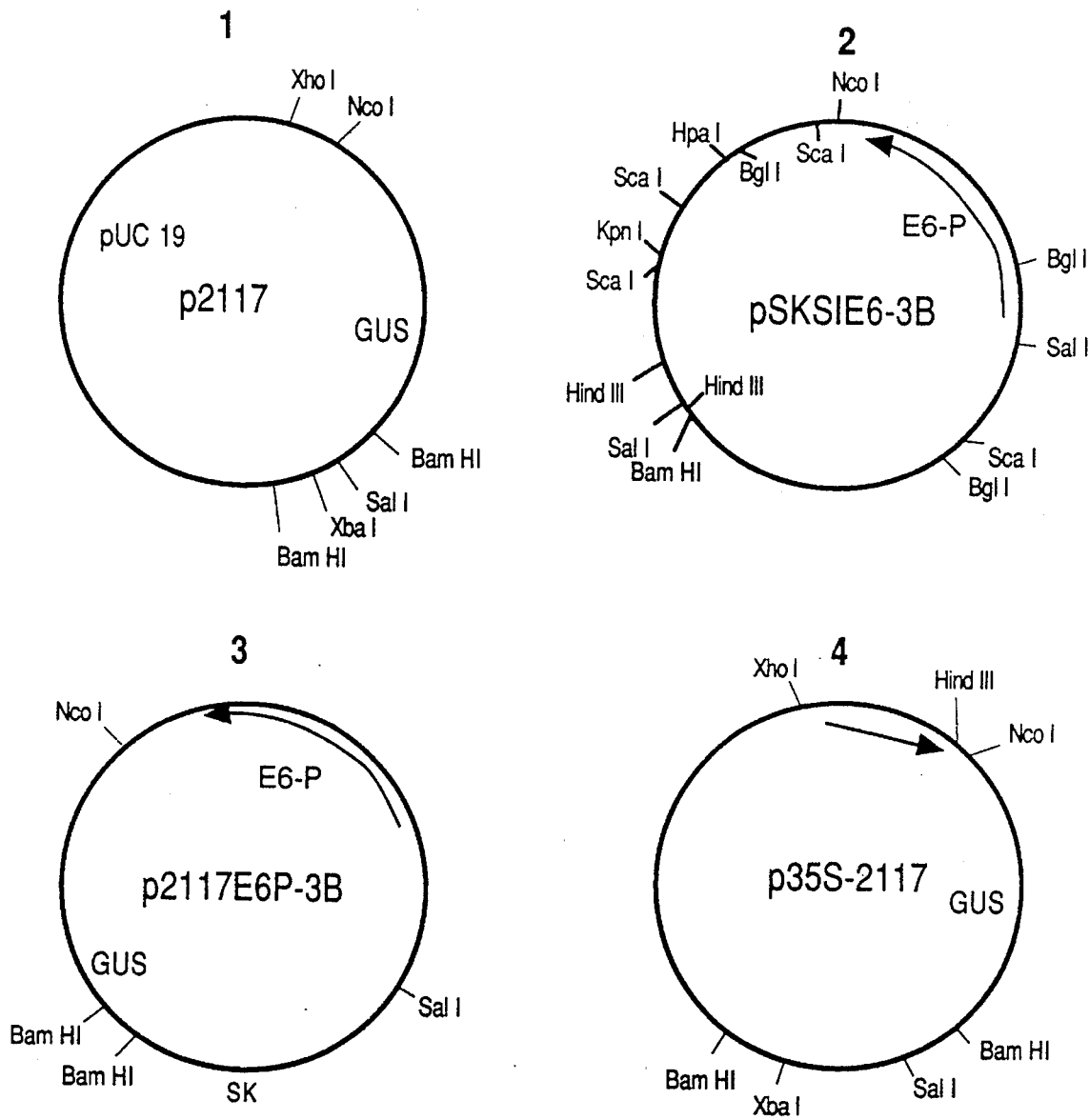
FIG. 3 is a diagram of plasmids useful in an assay for promoter activity.

FIG. 3 describes the plasmids used in that system. Basically, the system uses four plasmids. The first plasmid, p2117, contains a marker gene without a promoter. The second plasmid contains only the putative promoter. The third plasmid contains the putative promoter and a marker gene. The fourth plasmid, p35S-2117, contains a proven viral promoter and a marker gene. After bombardment of the test tissue with the different plasmids, expression by the third and fourth plasmids and not by the first and second indicates that the tested fragment has promoter ability. The Nco/Sal fragment (2.7 kb) of the E6 promoter and Bam HI/Bst BI fragment (2.2 kb) of the B8 promoter were subjected to this assay and found to have promoter ability. Cotton hypocotyl tissue was bombarded with the plasmids via particle-mediated methods, discussed below. Obviously, this system is not suitable for assaying whether or not the promoter is tissue-specific. In vivo plant experiments, in which the presence of the gene product in different tissues is examined, will determine whether the promoter is fiber-specific.

We investigated whether E6-3B promoter can be used to express a foreign gene in cotton fiber as follows: the E6 -3B promoter was fused with the coding region of a carrot cell-wall protein gene, extensin, and introduced into cotton. Various tissues of plants regenerated were examined by northern blots experiments to detect extensin RNA. We found that only fiber cells contain extensin RNA. John and Crow, *Proc. Natl. Acad. Sci. USA* 89: 5769–5773, 1992. These results support the claim that E6-3B promoter can direct expression of foreign genes in a tissue specific manner in transgenic cotton.

B. Bioplastic Genes (1) Ketothiolase

Thiolases catalyze the synthesis and cleavage of carbon-carbon bonds, are involved in the biosynthesis of terpenoid, steroid and macrolides and are involved in the degradation of fatty acids. The beta ketothiolases of *Z. ramigera* and *A. eutrophus* catalyze the condensation of two acetyl CoA groups to form acetoacetyl CoA. Beta-ketothiolases from other bacerial strains have also been studied. These strains include *A. beijerinckii* (Senior and Dawes, *Biochem. J.*, 134: 225–238 (1973) and *Clostridium pasteurianum* (Bernt and Schlegel, *Arch. Microbiol.* 116: 21–27: 1975).

The nucleotide sequence of the ketothiolase gene from *Alcaligenes eutrophus* is described in Peoples and Sinskey, *J. Biol. Chem.* 264: 15293–5297, 1989 (hereby incorporated by reference). We obtained *A. eutrophus* from ATCC and grew it under conditions described in Peoples and Sinskey, supra.

The coding region of the ketothiolase gene was cloned by PCR as follows: Two primers, MEJ288 and MEJ75 (SEQ ID NOs: 6 and 7) were used to amplify the ketothiolase gene from *A. eutrophus*. Primer MEJ288 contained an Xho I site and primer MEJ75 contained a Hind III site. The primers were used to amplify the coding region (1180 bp) of the ketothiolase gene. This product was then digested with Xho/Hind III. This resulting fragment was cloned into Xho/Hind III site of a vector containing an E6-3B promoter. The coding sequence of the ketothiolase gene, taken from Peoples and Sinskey (supra), is reported in SEQ ID NO: 23.

The ketothiolase gene PCR product was sequenced by Lofstrand Inc., Gaithersberg. The PCR product sequence differed from the published sequence at one position. Starting from the initiation codon, nucleotide C at position 671 was substituted by T in the PCR product. This substitution does not result in any amino acid change.

We also tested whether the PCR product can be transcribed and translated into a protein in an in vitro system. The plasmid containing ketothiolase gene was treated with a transcription/translation-coupled rabbit reticulocyte lysate system (Promega, Madison) and the radiolabeled products were size fractionated on a 15% SDS-polyacrylamide gel along with marker proteins (Amersham). Dried gels were then exposed to X-ray film at −70° C. for 2 hours. A protein of 40 kDa was observed, which is in agreement with the known molecular weight of ketothiolase. This experiment further confirms that the ketothiolase gene we have constructed will be properly transcribed and translated.

Additionally the transcription/translation was carried out in the absence of radiolabeled amino acid and the reaction mixture was assayed for ketothiolase activity as described by Nishimura et al. (*Arch. Microbiol.*; 116: 21–27, 1978). This test produced enzymatic activity above background. In order to confirm that the activity we obtained was due to the transcription/translation of the thiolase plasmid, we linearized the plasmid by digesting with restriction enzyme Sal 1. There are two Sal 1 sites in the thiolase coding region, at 418 bp. and 433 bp. Therefore, digestion with Sal 1 will result in the premature termination of transcription and translation. Only background activity was observed when the linearized plasmid was subjected to in vitro transcription/translation and thiolase activity measurements, indicating that the intact plasmid can direct synthesis of an active thiolase.

We used a prokaryotic expression system to measure the activities of PCR-cloned bioplastic genes. Plasmid DR 540 (Pharmacia LKB Biotechnology) is an expression vector containing a tac promoter (de Boer, H. et al., *Proc. Natl. Acad. Sci, USA*, 80: 21 (1983). The expression from this promoter can be repressed in a lacI+ host by lactose repressor. Isopropylthio-beta-galactoside (IPTG), which is an inducer of beta-galactosidase can be used to induce the expression from tac promoter. The ketothiolase gene was excised as an Xho I/Hind III fragment and treated with Klenow DNA polymerase to make the ends blunt. Bam HI linkers were added and the gene cloned into Bam HI-digested DR 540 plasmid. The orientation of the insert in DR 540 was determined by restriction site mapping. Independent clones harboring thiolase genes in the sense and antisense orientations were selected and cultures were grown overnight. The stock cultures were diluted and grown in the presence of inducer IPTG. Cells were harvested and thiolase activity measured in cell lysate. Cells harboring the gene in the sense orientation gave thiolase activity while cells with gene in the antisense orientation showed no activity. From these experiments we conclude that the PCR-cloned ketothiolase gene is functional and the one substitution that we observed is not detrimental to the enzymatic activity.

(2) Acetoacetyl CoA Reductase

The DNA sequence of acetoacetyl CoA reductase gene was reported in Peoples and Sinskey *J. Biol. Chem.*, 264: 15293–15297, 1989 (hereby incorporated by reference). The reductase gene was cloned by PCR amplification from *A. eutrophus* using MEJ76 and MEJ77 (SEQ ID NOs: 8 and 9). MEJ76 contains a Bam HI site and MEJ77 contains a Xba I site. This amplification created a 741 bp fragment that was cloned into Bam HI/Xba I sites of SK+ vector. This resulting plasmid is referred to as PHB-B. The coding sequence of the Acetocetyl CoA Reductase gene, taken from Peoples and Sinskey (supra), is reported at SEQ ID NO:24.

The PCR product of acetoacetyl CoA reductase was sequenced and compared with the published sequence. Four nucleotide changes were observed. Starting from the initiation codon, nucleotide "A" at position 433 was changed to nucleotide G. This would result in an amino acid change from lysine to arginine. A second change was detected at position 497 where a C was changed to a T in the PCR product. This will cause an amino acid sequence change from alanine to valine in the PCR product. Further, at position 556 nucleotide "A" was changed to a G. At position 557, a T was changed to C. These two changes result in a change of amino acid from isoleucine to alanine.

In order to test whether the PCR-produced acetoacetyl CoA reductase gene could be translated into a product with the correct molecular size, we conducted the transcription/translation-coupled reticulocyte lysate experiment. A protein of 27 kDa was obtained. The size of this product agrees with the known molecular weight of this enzyme.

The enzymatic activity of the acetoactyl reductase gene was tested in the transcription/translation coupled in vitro system (supra). No activity was detected. The gene was excised by digestion with Bam HI/Xba I and treated with Klenow polymerase to blunt the ends. Bam HI linkers were then added. The gene was then cloned into expression vector, DR 540 as a Ban HI fragment and orientation determined by restriction map analysis. Cells containing either sense or antisense plasmids exhibited no reductase activity after IPTG induction. Thus, it is apparent that the substitutions in the gene may have caused the loss of enzymatic activity of the protein. Therefore, we repeated the PCR cloning of reductase under PCR conditions to increase the fidelity of the system (Innis and Gelfand in *PCR Protocols*, Eds. M. A. Innis, D. H. Gelfand, J. J. Sninsky, T. J. White; pp. 1–12, 1990). Primers MEJ76 (SEQ ID NO: 8) and MEJ305 (SEQ ID NO: 10) and a second set of primers, MEJ76 (SEQ ID NO: 8) and MEJ304 (SEQ ID NO:11) were used along with 50 micromolar dNTPs, 0.5 unit of Taq polymerase and 5 µl of bacterial culture. Other conditions were similar to those described earlier (supra). MEJ304 and MEJ305 contain Bam HI sites. MEJ305 primes at the stop codon of the reductase gene while MEJ304 primes 99 bases downstream of the stop codon. Hence, the PCR product of MEJ76/305 will have only the coding region of reductase and is referred to as PHB-Bs, while the PCR product of MEJ76/304 will result in coding region and 99 bases of 3'untranslated region. The longer insert is referred to as PHB-B1.

The PCR products after Bam HI digestion were cloned into Bam HI sites of SK+ vector. After determination of orientations we conducted transcription/translation reactions with the genes in the SK+ vector. Both PHB-Bs and PHB-B1 were found to express active enzyme. We also cloned the PHB-B1 and PHB-Bs inserts into DR540. Cells containing sense orientation of the genes exhibited reductase activity while those with antisense genes showed no activity.

From these experiments we conclude that substitutions at nucleotide positions 433, 497, 556, 557 are detrimental to the activity of the reductase gene.

(3) PHB Synthase (PHB Polymerase) Gene

The DNA sequence of the PHB synthase gene is reported in Peoples and Sinskey *J. Biol Chem.*, 264: 15298–15303, 1989 (hereby incorporated by reference). The 1770 bp polymerase gene was cloned by PCR amplification from *A. eutrophus*. Four PCR primers, MEJ70-73 (SEQ ID NOs: 12–15) were used. PCR amplification using primers MEJ70 and 71 resulted in a 580 bp fragment while MEJ72 and 73 gave a 1200 bp fragment. The 580 bp fragment was digested with Eco RI/Bam HI and cloned into SK vector. This fragment contains an internal Bgl II site. The 1200 bp fragment as well as the SK vector containing the 580 bp fragment was then digested with Bgl II and Bam HI and the 1200 bp fragment was ligated to Bgl II/Bam HI sites. The orientation of the fragment in relation to the 580 bp 5' end was determined and clones containing the correct orientation were selected. This clone will be referred to as PHB-C1.

The coding sequence of the PHB Synthase gene, taken from Peoples and Sinskey, *J. Biol. Chem.*, 264: 15298–15303, 1989 is reported at SEQ ID NO: 25. The PHB synthase PCR product was sequenced. There were two nucleotide substitutions. First one was at position 103, counting from the initiation codon, where a T was substituted by a C. This substitution results in an amino acid change from serine to proline. The second substitution was at 1533 where a T was substituted by a G. This will not cause a change in amino acid composition.

In order to correct the mutation at position 103, we repeated PCR amplification of the 580 bp fragment using MEJ70/71 under more stringent PCR conditions (supra). The fragment was digested with EcQ RI and Nco I. This resulted in a 250 bp fragment that was cloned into Nco/Eco RI sites of SK+ vector and sequenced. We selected clones that showed no changes at position 103 or elsewhere and excised the insert by digesting with Nco/RI. Plasmid PHB-C1 was digested with Nco/RI and the large DNA fragment was gel purified. The above 250 bp fragment was then ligated to PHB-C1.

The translation product of PHB synthase gene was examined in a transcription/translation-coupled reticulocyte lysate system. The reaction product was found to be 64 kDa, which is in agreement with the known molecular weight of PHB synthase.

(4) Other Bioplastic-producing Genes

By "bioplastic-producing gene" we mean a gene that encodes a protein necessary or useful in creating bioplastics. Besides the genes necessary to produce PHB, other bioplastic-producing genes are equally suitable for the present invention. These genes may be presently known in the literature or may be identified in future work. What is necessary of the gene is that it encode a protein that controls bioplastic synthesis and that it be capable of expression in fiber cells.

Besides poly 3-hydroxybutyrate, bacteria are known to produce other bioplastic polymers, such as 3-hydroxyvalerate, 4-hydroxybutyrate or 5-hydroxyvalerate. Such copolymers have different thermoplastic properties than the 3-hydroxybutyrate monomers.

The fiber-producing plant should contain the substrate molecules necessary to create a bioplastic molecule. The PHB synthesis enzymes, ketothiolase, acetoacetyl-CoA reductase, and PHB synthase from *A. eutrophus*, can utilize a variety of substrates such as 3-hydroxybutyryl-CoA, propionyl-CoA, 3-ketovaleryl-CoA or 3-hydroxyvaleryl-CoA to produce copolymers (Haywood et al. *FEMS Microbiol. Lett.*, 57: 1–6 (1989). Mutant strains of *A. eutrophus* that produce copolymers from single unrelated carbon sources have been described (Steinbuchel and Pieper. *Appl. Microbiol. Biotechnol.* 37: 1–6, 1992).

The enzymes producing PHA, PHB and other polymers from different strains show different substrate specificities. (See Peoples and Sinskey, WO 91/00917). For example, PHB synthase from *Z. ramigera* is stereospecific for D-beta-hydroxybutyryl CoA while synthase from *A. eutrophus* can utilize other substrates such as D,beta-hydroxyvaleryl CoA. Recently, the PHA synthase gene from *Rhodococcus ruber* has been sequenced and shown to complement a PHB synthesis in PHB-negative mutant of *A. eutrophus* (Piper and Steinbuechel, *Microbiol. Lett.*, 96: 73–79, 1992). Thus, by engineering different bioplastic enzyme genes in cotton, one may be able to get a variety of different bioplastics in fiber. PHA synthase enzymes may be the most important in this regard. For examples, two PHA synthase genes have been identified in *Pseudomonas oleovarans* (See Peoples and Sinskey, WO 91/00917). *P. olevarans* produces PHA biopolymers from a broad range of carbon sources including n-alkanes, 1-alkenes, and fatty acids (Lageveen, et al. *Appl. Environ. Microbiol.* 54: 2924–2932, 1988; Brandl, et al. *Appl. Environ. Microbiol.* 54: 1977–1982, 1988). This enzyme does not incorporate beta-hydroxybutyrate. Thus, these enzymes may be advantageous for producing different biopolymers in fiber. The nucleotide sequence of PHA synthase 1 and PHA synthase 2 are given in Peoples and Sinskey WO 91/00917. PHA synthase 1 and 2 have a 68.6% similarity at the nucleotide level. PHB synthase of *A. eutrophus* shows 58.9 and 60.9% similarities with PHA synthase 1 and 2 of *P. olevarans*, respectively. Recently, a third PHA synthase gene has been identified from Rhodococcus ruber which uses glucose as sole carbon source to produce poly (3-hydroxybutyrate, 3-hydroxyvalerate) copolymers (Haywood et al., *Int. J. Biol. Macromol.* 13: 83–88, 1991). The sequence of PHA synthase of *R. ruber* is given in Pieper and Steinbuchel, *FEMS Microbiol. Lett.* 96: 73–80, 1992.

Ketothiolase and acetoacetyl CoA reductase genes are also being identified from various bacterial strains. For example, thiolase and reductase genes have been isolated and characterized from *A. ramigera*. Peoples et al. *J. Biol. Chem.*, 262: 97–102, 1987 presents the nucleotide sequences of the thiolase. Similarly, the reductase gene is reported in Peoples and Sinskey, *Mole. Microbiol.*, 3: 349–357, 1989.

Thus, as the genetic systems for the production of various bioplastics become known in bacteria, one may use genes for different bioplastic enzyme systems or enzymatic pathways to use different carbon sources to produce more useful copolymers. These systems can then be adopted into the present invention to synthesize bioplastics in cotton fiber. The section below discusses how to evaluate whether or not a given DNA sequence is useful in the present invention to create altered cotton fiber.

C. Construct Formation

Once the desired gene and fiber-specific promoter are identified, it is necessary to combine these elements into a construct so that the fiber-specific promoter can control the transcription of the gene. This is typically done by standard molecular biological techniques. Preferably, the bioplastic gene is ligated downstream from the fiber-specific promoter in a plasmid or viral vector. We envision that an altered cotton fiber might require more than a single heterologous gene. Therefore, the cotton plant might advantageously be transformed with constructs containing more than one bioplastic gene or more than one construct.

Preferably, the coding regions of bioplastic genes will be fused with fiber-specific promoters in such a manner that transcription will occur from an untranslated leader sequence contained in the 3' end of the promoter. This untranslated region also was identified from fiber genes. At the 3' end of the coding region of the bioplastic gene, a 3' untranslated region of a fiber gene is preferably fused. This region contains a poly-(A) additional signal that enables transcription to stop. Sequence of the 3' untranslated region that we used in our bioplastic gene expression vector is shown in SEQ ID NO: 16 and was identified from the fiber-specific geonomic clone pSKSIE6-3B. The 3' untranslated regions of other plant genes would also be suitable.

As an added precaution that correct transcription stop will occur, we added a nopaline synthase (Nos) poly-(A) addition signal (Depicker et al., *J. Mol. Appl. Genet.*, 1: 561–573, 1982). Preferably, a sequence such as this should be used to correctly process the 3' end of the message. The Nos poly-(A) sequence has been proven to function as an authentic plant transcription stop signal (McCabe et al. *Biotechnology*, 6: 923–926, 1988). The fragment containing the 3'-end of E6 gene and the Nos poly-(A) fragment were cloned into a number of restriction sites in the SK vector and are shown in FIG. 5.

Most transformation methods work on a statistical basis. A certain low percentage of the target cells will become transformed. To identify these transformed cells, it is useful to insert a marker or selection gene in the construct.

A marker gene which has been found useful in such plant transformation experience is the GUS gene as described by Jefferson et al., *EMBO J.* 6: 3901–3907 (1987). The GUS gene encodes the enzyme beta-glucuronidase, which can be expressed in plant cells. The expression of the GUS gene can be determined, in a tissue destructive but convenient histochemical assay of plant tissues. The product of the GUS gene will change the color of a substrate, 5-bromo-4-chloro-3-indolyl glucuronide, to blue in an in situ assay in plant tissues. Thus, the use of a GUS gene provides a convenient colorimetric assay for the expression of introduced DNA in plant tissues by phenotypic analysis in the plant tissues.

In a typical transformation process, the desired gene of interest sought to be expressed in the plant could be coupled in tandem in a single genetic construct with the GUS gene. The coupled tandem genetic construct could then be transformed into plant tissues and the resultant plant tissues would be analyzed for expression of the GUS enzyme in the target plant tissues to identify transgenic tissues.

Another way to identify the presence of the construct in a plant cell is to use a selectable marker gene. A selectable marker is one that conditions for a trait in the transformed plant cells which can be selected by the exposure of the plant tissues to a selection agent. Suitable selectable markers would be antibiotic resistance genes or herbicide resistance genes which, when inserted in some cells of a plant in culture, would imbue those particular cells with the ability to withstand exposure to the antibiotic or the herbicide which would kill all the nontransformant cells in the culture. Selectable markers are generally preferred for plant transformation events, but are not available for all plant species.

D. Transformation (1) In General

We chose to use accelerated particles to transform cotton with the DNA constructs. A style of apparatus for accelerating such particles has been described in detail in U.S. Pat. No. 5,015,580 (hereby incorporated by reference). In brief, small metal particles are coated with nucleic acid material and accelerated into target cells. By an unknown mechanism, a certain percentage of the target cells will incorporate the nucleic acid.

Other particle acceleration apparatus, such as the commercially available BioRad (Biolistics) PDS-2000 particle acceleration instrument, will be suitable for the present invention. Other non-accelerated particle methods are also suitable. Such methods include electroporation, viral vectors, and Agrobacterium-mediated transformation.

Stable integration and expression of foreign genes in cotton plants has been demonstrated and repeated. Umbeck et al., *Bio/Technology*, 5[3]: 263–266 (1987); Firoozabady et al., *Plant Mol. Biol.*, 10: 105–116 (1987). In each of these references, the transformation of cotton tissues is accomplished by Agrobacterium infection and regeneration. Although a lengthy process, the Agrobacterium-mediated transformation of cotton has also been practiced by other laboratories and can now readily be replicated by those of ordinary skill in plant genetic engineering.

It is to be understood, however, that new methods for the transformation of cotton plants and lines are being studied, and that the transgenic cotton plants and lines with introduced bioplastic genes will prove advantageous and useful regardless of the method of transformation of the original tissues. The description below suggests a preferable method of transformation.

(2) Surface Sterilization

We have developed a cotton transformation system that is particularly advantageous for the practice of the present invention. The process begins with commercial cotton seed, which must be sterilized. In our example, we used DP-50 cotton seeds, although other varieties would be equally suitable. We chose DP-50 because it is a cotton variety with good growing characteristics but a coarse fiber.

A sieve beaker system is autoclaved. A sieve beaker system is a beaker with dozens of holes drilled in its bottom that can be nested inside a non-drilled glass beaker. It is also useful to utilize a third sterile beaker for rinsing the seeds so that the sieve beaker can be rested in the sterile beaker while discarding wash water.

The sieve beaker is filled with cotton seeds. The beaker into which the sieve beaker is nested is then filled with a mixture of 50% Chlorox bleach so as to cover the seeds. The seeds are allowed to rest within the bleach solution for three minutes. The bleach is drained and the seeds are then rinsed five times with distilled water.

The surface sterilized cotton seeds are then placed in a sterile glass beaker. A cotton antibiotic sterilization medium is added to the beaker at twice as much volume as there are seeds. This medium consists of sterile distilled water to which has been added carbenicillin at 200 mg per liter, cefotaxime at 125 mg per liter, and 30 mg each of —BRAVO WP™ fungicide—, —BENLATE 50 DF™ fungicide— and —CAPTAN 50 WP™ fungicide— per liter. The seeds are incubated in the sterilization medium for three to four hours in the dark at room temperature.

Then the seeds are drained by pipette. The beaker is refilled with fresh cotton antibiotic sterilization medium and the seeds are incubated for an additional three hours.

The seeds were then drained and incubated overnight at 15° C. in the dark to germinate. If germination proceeds appropriately, the seed germination could be stopped by refrigeration at 4° C., for up to three days following the germination process.

(3) Seed Dissection

After the germination of the seeds, or the removal of the germinated seeds from storage, seeds are selected that are just beginning to germinate. Overly germinated or ungerminated seeds are discarded. The proper stage of germination is defined as fully imbibed seeds with one to four millimeters of the radicle exposed. Under sterile conditions, the seed axis is removed out of the seed. This is done by manual manipulation with gloved hands to remove the seed axis from both of its cotyledons and its seed coat. The process is relatively easy to perform with practice. It is possible to readily develop the ability to pop the seed coat axis apart from the seed, without damaging the seed axis, or leaving any of the cotyledon on the seed axis.

The excised seed axis is then washed in three to four rinses of sterile distilled water. The washed but undissected explants are either dissected immediately or stored by plating on standard OR ccb medium made with fresh benzylaminopurine or BAP, but no NAA. This media is described by Barwhale et al., *Planta*, 167, pp. 473–481 (1986), but without the NAA hormone. The explants are plated on the agar surface by being laid on their side. The excised embryonic seed axis plated on the agar medium are incubated at 15° C. in the dark overnight.

(4) Exposing The Meristem

The washed seed axis explants are now ready for micro dissection to expose the meristems of the seed axes. This dissection is performed under sterile distilled water and with sterile tools. The dissection consists of removing the embryonic leaf, or leaves if there is more than one, that obscure the meristem on each of the excised seed axes. The fully dissected explants are transferred to another petri dish containing sterile distilled water.

(5) Pre-Blast Hormone Treatment

After all the dissections are completed, the explants are again washed in three to five rinses of sterile distilled water.

The free water is removed by pipette after the final rinse. The treated explants are then laid on their side on the surface of standard OR ccb medium made with fresh BAP but not NAA. The explants are incubated overnight, or for 24 hours maximum, at 15° C. in the dark. The treated excised embryonic axes with exposed meristems are now ready for the accelerated particle transformation blast.

(6) Genetic Material And Carrier Particle Preparation

Ten milligrams of amorphous crystalline gold powder, or of an equal mixture of 1–3 micron gold spheres and crystalline gold powder is measured into the bottom of a 1.5 ml Eppendorf microfuge tube. Care is taken to ensure that the gold did not spill on the sides of the tube, since that would make it difficult to resuspend the gold due to the small volumes used in the preparation process. 100 μl of 0.1M spermidine (free base) is added to this microfuge tube and the microfuge tube is vortexed well. 1 to 20.0 μg of double-stranded DNA is then added to the microfuge tube and the tube is then vortexed gently but completely. While the DNA/carrier particle mixture is gently vortexed, 100 μl of 2.5M $CaCl_2$ is added to the tube. The vortex is stopped, and precipitation is permitted for 10 minutes at room temperature. The preparation could be stored at this point for some time. Shortly before use, the mixture of DNA and carrier particles is given a brief spin in a microfuge. The cleared supernatant is removed completely, and the precipitant consisting of the DNA and carrier particles is resuspended in 20 ml of 100% ethanol. The resuspended DNA and carrier particle mixture is then sonicated in a water bath sonicator for two to three brief one second exposures. The resulting suspension is then coated onto the carrier sheet, at a calculated rate of 0.05 milligrams per square centimeter of the carrier sheet. After allowing the gold to settle, the excess ethanol is drained away and the sheet is dried. These preparations of DNA and carrier beads are made fresh daily.

(7) Blasting

At this point in the process, the carrier sheets are placed upon the apparatus for the blasting process. This procedure and apparatus are similar to that disclosed in U.S. Pat. No. 5,015,580, which is hereby incorporated by reference. The cotton explants are plated on 12% xanthan gum target plates. Using the normal germination and pre-blast hormone treatments described above, typically 25 explants are found to fit on each of the target surface within the blast area.

The parameters used for the particle-mediated transformation blast itself includes a relatively high electric discharge voltage through the gun, typically in the range of 15–25 kilovolts. The standard voltage used is 18 KV. The voltage is adjusted to achieve a level of impact on the treated axes such that the rate of survival of the meristems is between 40% and 90%. In other words, the blast force is adjusted to a level such that at least some of the meristems are rendered non-viable by the process. The blasting experiments are conducted at 350 milliliters of mercury, with helium introduced at a rate of 1.5 liters per minute at atmospheric levels, and approximately 5.0 liters per minute under the vacuum.

Each of the target tissues is blasted once or twice during the same day. Target tissues blasted twice in the same day are blasted once in the morning and once in the afternoon, with the explants stored between successive blasting procedures in a moist chamber at approximately 28° C. in the dark. The target tissues are placed in the dark immediately after each blasting exposure.

(8) Post-Blast Protocol

The explants are now removed from the target surface, and plated in a normal orientation on OR ccb medium made with fresh BAP but no NAA. Care is taken not to expose the explants to excessive light. Care is taken to keep the meristem from contact with any media, and no wet plates are utilized. The fresh explants are plated and then incubated at 28° C. in the dark for one to two full days.

One day after the blasting, a preliminary assessment of transient enzyme activity is conducted on the resultant tissues. The assay is conducted at this time to check for the quality of the bead preparation protocol, and also to look specifically at the number of transformation events in the meristem, a rough approximation of which can be made by checking the transient activity of the explants at this stage. Although due to the heavy damage from the blasting process 20 to 60% of the meristems are sufficiently damaged so as to never produce shoot, those same damaged meristems will, upon assay, exhibit excellent transient gene activity particularly of the GUS gene using this procedure. Thus, the tissues can be assayed at this step for the percentage of GUS activity, even though shoots are not yet evident on the meristems subjected to the procedure.

Following the initial post-blast incubation on the medium described above, the cotton explants are transferred to the dextrose-based woody plant medium (WPM), minus BAP plus carbenicillin and benomyl, in plantcons again under low light. The WPM medium mixture, based on Lloyd and McCown, *Proc. International Plant Propagation Soc.*, 30: 421–427 (1981) is prepared as follows: $NH_4NO_3$ (400 mg/L), $Ca(NO_3)_2.4HOH$ (556 mg/L), $K_2SO_4$ (990 mg/L), $CaCl_2.2HOH$ (96 mg/L), $KH_2PO_4$ (170 mg/L), $H_3BO_3$ (6.2 mg/L), $Na_2MoO_4.2HOH$ (0.25 mg/L), $ZnSO_4.7HOH$ (8.6 mg/L), $CuSO_4.5HOH$ (0.025 mg/L), $FeSO_4.7HOH$ (27.8 mg/L), $Na_2EDTA$ (37.3 mg/L), Thiamine.HCL (1.0 mg/L), Nicotonic acid (0.5 mg/L), Pyridoxine.HCl (0.5 mg/L), Glycine (2.0 mg/L), Myo-inositol (100 mg/L), Dextrose (20 g/L), Agar (3.0 g/L), Gelrite (1.1 g/L), Calcium gluconate (1.29 g/L), Carbencillin (200 mg/L) and Benomyl (60 mg/L). The tissues are incubated at 28° C. in the dark for one to seven days.

Following the culturing steps outlined above, the plantcons are then moved to full light exposure so as to induce shoot development in the tissues under cultivation.

(9) Identification of Transformant Events

The plantcons are then moved to a cultivation chamber and exposed to 16 hour light periods at 28° C. A number of cultured explants then proceed to exhibit shoot elongation and development from the plated tissues. It then becomes necessary to evaluate the growing shoots to ascertain the level of germ line transformation events which are achieved through this process. The assay procedure is conducted at such a point that the shoots each have developed their first leaves. The outermost one-third to one-half of each leaf is then cut off completely across the leaf through the midrib. The leaves are then assayed for GUS activity to identify GUS-positive expressing plants.

At this point, the quality of the event is characterized depending on the level of GUS activity in the leaf. Some of the leaves exhibited only uneven or irregular GUS expression, indicating chimeric plants. Based on the results below and experience with other plant systems, we have observed and verified that a transformation of the vascular system, as exemplified by the leaf petiole, correlates very well with the occurrence of a germline transformation event. Some of the leaves seemed to be totally blue, indicating putatively clonal transgenic plants. If the plant is characterized as germline transformed, the plant is transferred into rooting conditions and grown out in the greenhouse. For chimeric plants, the plant is pruned to just above the transformed leaf so as to force the axillary bud to grow from the transformed area of the plant after which it is retested.

For plants that tested negative, the leaves are removed, and the plants are cultured until newly formed leaves are regenerated. Tests are again conducted. This process is repeated three times before a final negative determination for the plants is made.

The entire process as described above, from initial plating of the seeds to the recovery of an initial generation transgenic plant requires approximately three to five weeks. Based on the initial results as described above, we expect that approximately one mericlonal transgenic plant will occur per approximately 100 to 500 meristems exposed to the blasting process. Of the mericlonal plants produced from the process, approximately 0.1–1.0% will be found to have transformed germ lines. Thus, although the yield may seem low, this process allows for the relatively rapid and more inexpensive generation of large numbers of transgenic plants than other procedures because the process can be performed quickly. The transgenic plants will transmit the inserted genes by Mendelian inheritance, and the process can be performed directly on elite cotton lines, even Sea Island and Pima lines, which are resistant to tissue-culture methods.

(10) Examination of Fiber

When the transgenic cotton plant is able to produce mature fiber, the fiber must be examined in order to determine whether advantageous alterations have occurred. Cotton fiber length is genetically determined and therefore varies from cultivar to cultivar. Commercially, American upland cottons are classified as either short staple (up to 1 inch; 2.5 cm), medium staple (1-1/32 to 1-3/32 inch; 2.63–2.78 cm), or long staple (over 1-1/8 inch; over 2.86 cm). Instruments such as fibrograph and HVI (high volume instrumentation) system are used to measure the length of the fiber. HVI instruments compute length in terms of "mean" and "upper half mean" (UHM) length. The mean is the average length of all the fibers while UHM is the average length of the longer half of the fiber distribution.

Fiber strength is usually defined as the force required to break a bundle of fibers or a single fiber. In HVI testing the breaking force is converted to "grams force per tex unit." This is the force required to break a bundle of fibers that is one rex unit in size. In HVI testing the strength is given in grams per tex units (grams/rex). Fibers can be classified as (1) low strength, 19–22 gms/tex, (2) average strength, 23–25 gms/tex, (3) high strength, 26–28 gms/tex, and (4) very high strength, 29–36 gms/tex.

The micronaire reading of fiber is obtained from a porous air flow test. The test is conducted as follows: a weighed sample of cotton is compressed to a given volume and controlled air flow is passed through the sample. The resistance to the air flow is read as micronaire units. The micronaire readings reflects a combination of maturity and fineness. Since the fiber diameter of fibers within a given variety of cotton is fairly consistent, the micronaire index will more likely indicate maturity variation rather than variations in fineness. A micronaire reading of 2.6–2.9 is low while 3.0–3.4 is below average, 3.5–4.9 is average and 5.0 and up are high. For most textile applications a micronaire of 3.5–4.9 is used. Anything higher than this is not desirable. Of course, different applications require different fiber properties. A fiber property that is disadvantageous in one application might be advantageous in another.

In addition to the above-described measurements, transgenic fibers containing bioplastics will be subjected to a number of different measurements. Rate of imbibition, water content, moisture regain and water bound to cellulose molecules, and water holding capacity will be measured using such instruments as a gravimetric absorbency testing system (M/K Testing System Inc., Danvers). These tests are described in detail by American Society for Testing and Materials (ASTM standards, section 7 Vol. 0701 and 0702, Ed. Roberta A. Storer).

Additionally, tests for shrinkage and elastic properties and examination of thermal characteristic such as surface temperature difference using infrared thermography would be useful. Actual human wear trials can be undertaken. Such measurements are routinely done at various textile and USDA laboratories.

EXAMPLES

A. E6-3B Promoter

Plasmid pSKSIE6-3B contains the promoter of fiber-specific gene E6-3B. We have demonstrated that a 2.7 kb Sal (Mbo I)/NCo I fragment contains a functional promoter by linking the promoter to a marker gene, GUS, and observing transient expression. Subsequently, we have generated stable transgenic cotton plants using this promoter upstream from a carrot extensin gene and demonstrated that the extensin gene was expressed in a tissue-specific and developmentally regulated fashion in cotton fibers (John and Crow, *Proc. Natl. Acad. Sci.*, 89: 5769–5773, 1992).

Next to the unique Nco site in the E6-3B promoter is a Bst XI site. In order to construct a promoter fragment for bioplastic gene expression, we removed the Nco. site. For this removal, the plasmid was digested with Bst XI and the ends repaired by treatment with T4 polymerase. This procedure destroyed the Nco site, and the resulting ends were blunt. We added Sal I linkers to the fragment (2.7 kb). After digestion with Sal I and gel purification, this fragment was then ligated to the Xho I site of $SK^+$ vector. Clones containing the promoter in both orientations were identified by Sekar SDS-gel electrophoresis and subsequent plasmid analysis by restriction mapping and sequencing.

A clone designated as E6-3B/SaC will have the promoter in such an orientation that when the coding region of a gene is ligated at any site between Sal I and Sac I in the SK vector, transcription will be towards the Sac I site. Similarly, when a clone is designated as E6-3B/Kpn the promoter is such an orientation that the transcription is towards the Kpn site. Thus, genes can now be ligated to a number of restriction sites downstream from the promoter.

In addition to the two vectors described above, we modified the SK+plasmid to include either an Nde or an Nhe restriction site at a unique Nae site in the fi phage intergenic region. This was done to create a new unique site for inserting marker genes. The Nae I site is about 340 bp away from the Sal/Xho sites where the E6 promoter is inserted. The SK+ vector was digested with Nae and phosphorylated Nde or Nhe linkers were ligated to the Nae site. The protocol for addition of linkers is well established and is described in *Current Protocols in Molecular Biology* (supra). This procedure resulted in two modified vectors, one containing a unique Nde site and the other containing an Nhe site. However, addition of these sites may have disabled the single-strand-forming ability of these phagemids.

These two vectors were digested with Xho I and the E6-3B promoter fragment was ligated into this site. These constructions resulted in E6-3B/Sac and E6-3B/Kpn plasmids and have the additional property of having unique sites away from the cloning sites for marker gene addition.

B. B8 Promoter

We have characterized a fiber-specific promoter from pSKSIB8. A 2.2 kb Bam HI/Bst BI fragment contained a functional promoter by transient expression analysis of the GUS gene. The promoter was modified to include two restriction sites at the 3' end next to a unique Bst BI site for convenient cloning. The Bst BI site is 120 bp from the putative initiation codon of B8 gene. We replaced the 120 bp region with a DNA fragment that contained an Eco RI and Bam HI sites. This was accomplished by PCR using primers MEJ 117 and MEJ 282. The sequences of these primers are presented in SEQ ID NOs: 17 and 18.

A plasmid containing the B8 promoter and a GUS marker gene, pSKB8-GUS was digested with Bst BI and Eco RI and a 5.2 kb fragment was gel purified. The PCR product was similarly digested with BstBI and Eco RI and ligated to the 5.2 kb fragment. The promoter can be excised as a Bam HI or Xba/Eco RI fragment. Furthermore, the Bam HI fragment was blunt-ended and Sal I linkers were added. The sal fragment was then ligated to the Xho I site of SK vector and clones containing the promoter in different orientations were selected. When the transcription is towards Sac I site, the B8 promoter is designated as B8/Sac, whereas when it is towards Kpn site it is designated as B8/Kpn.

C. Cloning of 3' Untranslated Region and Poly-(A) Addition Signal.

Functional genes contain a 3' untranslated region next to the coding region. This region contains the stop signal for the end of transcription. In addition, the 3' untranslated region may also influence the translation or stability of the transcripts.

Figure 4:
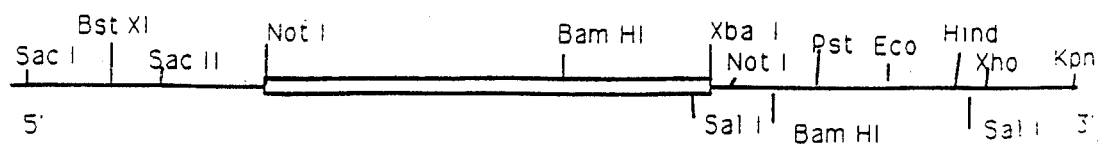
FIG. 4 is a diagram of E6-3B 3' end along with Nos (A) fragments.
Figure 4:
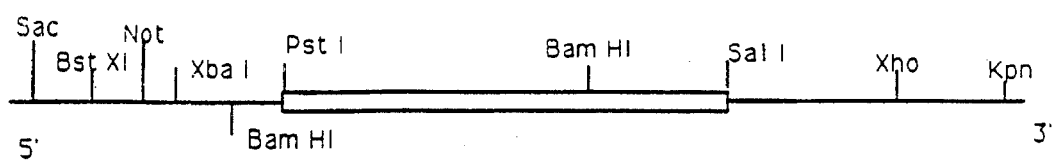
Figure 4:
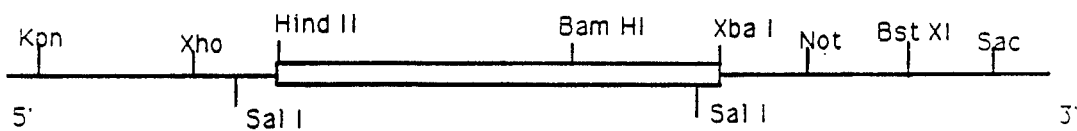

In order to provide a 3' untranslated region to the bioplastic genes, we cloned a DNA fragment from the 3' end of the fiber gene E6-3B from clone pSKSIE6-3B using primers MEJ35 and MEJ36 (SEQ ID NOs: 19 and 20) and PCR amplification. The resulting DNA (313 bp) was digested with Hind III and Bam HI and cloned into SK+ vector. The poly (A) addition signal from nopaline synthase was added as a Bam HI/Xba I fragment. Furthermore, in order to facilitate gene cloning, we made two other constructs containing the E6-3B 3' end along with the Nos A sequence as a single fragment. For these constructs, the E6-3B 3' end and the Nos A sequence were excised as a single fragment by Hind III/XbaI. The ends-were repaired by T4 polymerase. Not I linkers were added and cloned into an SK+ vector at the Not I site. A third fragment was cloned after PCR amplification using primers MEJ 207 (SEQ ID NO: 21) and DR112 (SEQ ID NO: 22). The PCR product was cloned into the SK+ vector. The 3' end sequence can now be excised from these three plasmids by a number of restriction sites as required for various cloning strategies. A schematic representation of these fragments is shown in FIG. 4. The open boxes signify the E6-3B 3'-end and the NOS A sequence. In the description of the cloning, the Nos A poly(A)-addition signal along with the E6-3B 3'-end will be referred to as the "3'-end".

D. Cloning of Bioplastic Genes.

1. Cloning of the Ketothiolase Gene and Expression Vector Construction With the B8 Promoter To construct an expression vector of ketothiolase with B8 promoter, the following cloning strategy was used. The 1180 bp PCR product from primers MEJ288/MEJ75 (SEQ ID NOS: 6 and 7) was digested with Xho I and Hind III. The purified product was then ligated with an SK+-Nde vector linearized at the Xho I and Hind III sites. The resulting plasmid was then digested with Xho I and a Sal I fragment of B8 promoter was added at the Xho I site. The orientation of the promoter in relation to the thiolase gene was determined and the correct plasmid was isolated. A 3' end was then inserted as a Not I fragment and the orientation was determined.

2. The Ketothiolase Gene With the E6-3B Promoter.

The Xho/Hind III ketothiolase fragment was ligated to the Sal I/Hind III site of E6-3B/Sac vector. The 3'-end fragment was then added at the Not I site, in a manner similar to the above construct.

3. Acetoactyl CoA Reductase With the B8 Promoter

The SK+ vector (PHB-B1) containing the 831 bp reductase gene obtained by PCR with MEJ76/MEJ304 primers (SEQ ID NOs: 8 and 11), as described above, was digested with Eco RI and Xba I. The fragment was gel purified and cloned into Eco RI/Xba I sites of B8/Sac vector. The 3'-end fragment was then added at the Not I site and the orientation was determined. Similarly, the insert from PHB-Bs was also cloned into B8 vector.

4. Acetoactyl CoA Reductase Gene With the E6-3B Promoter.

An SK vector containing E6-3B/Sac promoter was selected. The reductase gene as a Bam HI fragment was ligated to the E6-3B/Sac plasmid at the Bam HI site. The 3'-end fragment was then added at the Not I site.

5. Cloning of the PHB Synthase Gene and Construction of Expression Vector With the B8 Promoter.

The 3'-end was added to a B8/Sag vector as a SaCl/Xba I fragment. The SK+ plasmid containing PHB synthase (PHB-C1) was then digested with Cla I/Xba I. The 1770 bp fragment was then gel purified and cloned into the above B8/Sac vector, containing the 3'-end.

6. PHB synthase Gene With the E6-3B promoter.

The 3'-end was ligated to the E6-3B/Sac promoter vector at the Sac I/Xba I sites. The synthase gene was then ligated to the Cla I/Xba I sites of this plasmid. An internal Cla I site of the promoter is not cleaved due to methylation.

E. Marker Gene GUS

The GUS gene was added to the plasmids containing bioplastic genes to follow transformation events during regeneration of transgenic plants. A cauliflower mosaic virus 35 S promoter has been shown to direct the expression of this gene in plants. (McCabe et al., *Bio/Technology*, 6: 923–926, 1988).

In preliminary experiments we have observed that when three plasmids each containing one bioplastic gene each were mixed and bombarded into cotton, as described above, the resulting plants contained all three genes. Therefore, it may be possible to generate transgenic cotton containing all three genes by mixing one plasmid containing a bioplastic gene with a GUS marker gene and two plasmids containing bioplastic genes without marker genes. Since the marker gene is driven by a constitutive 35 S promoter, it may be advantageous to avoid generating plants containing three copies of the marker gene. Thus, we have made bioplastic genes with and without marker genes so as to mix them in different combinations.

The GUS gene can be excised from plasmid 2117 (FIG. 4) by digesting with Sal I and Xho I. The ends of the 1.8 kb fragment were treated with T4 polymerase and Nde I and Nhe I linkers were added in duplicate experiments. Similarly, the SK vector was digested with Nae I in duplicate experiments and then treated with phosphatase to prevent self-ligation. The linearized SK vectors were then ligated with Nhe I and Nde I linkers in duplicate experiments. Recombinant clones containing new Nhe I and Nde I sites were selected and were used for ligation of Bioplastic-producing genes described above. The GUS gene can now be ligated into Nde or Nhe sites.

F. Plant Transformation

We have established successful particle bombardment-mediated cotton transformation parameters. We have generated transgenic plants containing genes for carrot extensin (a hydroxy proline-rich cell wall protein); parathione hydrolase (a bacterial enzyme capable of removal of coumapos from waste water) and plant hormones. In each of these cases the proteins have been expressed in a fiber-specific manner. Thus, validation of the transformation protocol, construction of cotton expression vectors, as well as specificity of fiber promoters have been achieved.

Transgenic cotton plants were generated using the parameters described above. 15 transgenic plants were found to contain bioplastic genes. In five of the plants we demonstrated that RNAs for bioplastic genes are being transcribed. Mature fibers from these plants will be tested for presence of bioplastics and modification of the cotton fiber.

G. Enzymatic Determination of Beta-ketothiolase.

It may be necessary to examine transgenic cotton cells for the presence of active products of the bioplastic-producing genes. A common assay for ketothiolase is the following:

A. eutrophus cultures were grown at 30° C. for 40 hrs in nutrient broth media. The cells were harvested by centrifugation and washed three times with ice cold water. The cells (0.3 gm wet weight) were frozen in liquid nitrogen and pulverized in a mortar. Two ml of extraction buffer (20 mM Tris-HCl, pH 8.0.; 5 mM EDTA; 5 mM beta mercaptoethanol; 25 µg/ml phenyl methyl sulfonyl fluoride and 5% glycerol) were added. The mixture was homogenized and the lysate was centrifuged to remove cell debris.

Aliquots of the lysate were assayed for ketothiolase as described by Nishimura et al. (*Arch. Microbiol.* 116: 21–27, 1978) based on the observation that beta-ketothiolase catalyzes the cleavage of acetoacetyl-CoA. The reaction is monitored at 303 nm. Reaction mixture contained 100 mM Tris-HCl, pH 8.0, 50 mM $MgCl_2$, 0.07 mM acetoactyl CoA and bacterial lysate. The reaction mixture was equilibrated at room temperature for 3 min and monitored at 303 nm. At this time point, CoA was added (0.07 mM) and the decrease in acetoactyl CoA was measured. The millimolar extinction coefficient for acetoactyl CoA is 16.9 (Middleton, *Biochem. J.;* 139: 109–121, 1974). One unit of ketothiolase catalyses the cleavage of 1.0 micromole of acetoactyl CoA in 1 min.

H. Enzymatic Assay for Acetoactyl CoA Reductase.

Acetoactyl CoA reductase was assayed as described by Saito et al., *Arch. Microbiol.;* 114: 211–217, 1977. The reaction mixture contained 100 mM Tris-HCl, pH 8.00; 0.12 mM NADPH, and bacterial lysate. The mixture was preincubated at room temperature for 3 min. and monitored at 340 nm. Acetoactyl CoA was added (0.02 mM) and the decrease in NADPH was measured at 340 nm. for 5 min. The millimolar extinction coefficient for NADPH is 6.22. One unit of acetoactyl CoA reductase catalyses the oxidation of 1.0 micromole of NADPH in 1 min.

I. Protein Assay.

Protein concentrations were determined by the method of Bradford (*Anal. Biochem.;* 72: 248–254, 1976) using the BioRad micro-assay method and bovine serum albumin as the protein standard.

J. Enzymatic Determination From Plant Extracts.

The transgenic plants containing bioplastic enzymes can be assayed in a similar fashion as described for the bacterial source. The extraction buffer was modified to contain 0.01% soluble polyvinylpyrrolidone.

K. Assay for PHB

In addition to the enzymatic detection of ketothiolase and acetoactyl CoA reductase, one can detect PHB by gas chromatography, by gas chromatography-mass spectrometry analysis or by epiflourescence microscopy after staining with Nile Blue A. These methods have already been used to detect PHB in transgenic plants (Poirier et al., *Science,* 256: 520–523, 1992.)

L. Analysis of Transgenic Plants Containing Bioplastic Genes.

We have generated 15 plants containing the bioplastic genes. DNA from these plants was tested by PCR and the presence of all three bioplastic genes was confirmed in eleven of the plants. The remaining plants contained only two genes each. Young fibers from these plants were tested by PCR analysis of RNA. Five of the plants expressed RNA for all three bioplastic genes. These results are indications that we are successful in incorporating and expressing bioplastic genes in cotton.

I claim:

1. A cotton plant comprising in its genome heterologous genetic constructs encoding ketothiolase, acetoacetyl CoA reductase, and PHB synthase, wherein each construct comprises:
    (a) a fiber-specific promoter isolated from cotton plants; and
    (b) a coding sequence encoding a bioplastic-producing enzyme that catalyzes the production of a PHB bioplastic molecule from substrates present in the fiber-producing plant,
    wherein the coding sequence is selected from sequences encoding ketothiolase, acetoacetyl CoA reductase, and PHB synthase,
    wherein the promoter is operably connected upstream from the coding sequence; and
    (c) a transcriptional termination sequence operably connected to the coding sequence.

2. The plant of claim 1, wherein the construct additionally contains a marker sequence.

3. The plant of claim 2, wherein the marker sequence is for the GUS gene.

4. The plant of claim 1, wherein the sequence of the fiber-specific promoter is SEQ ID NO: 4.

5. The plant of claim 1, wherein the sequence of the fiber-specific promoter is SEQ ID NO: 5.

6. The plant of claim 1 wherein the plant is DP-50 cotton.

7. The plant of claim 1 wherein the coding sequences are SEQ ID NO: 23, so that an enzyme with ketothiolase activity is produced; SEQ ID NO: 24, so that an enzyme with acetoacetyl CoA reductase activity is produced; and SEQ ID NO: 25, so that an enzyme with PHB synthase activity is produced.

8. Seeds of the plant of claim 1.

9. A cotton plant cell comprising in its genome heterologous genetic constructs encoding ketothiolase, acetoacetyl CoA reductase, and PHB synthase, wherein each construct comprises:
    (a) a fiber-specific promoter isolated from cotton plants; and
    (b) a coding sequence encoding a bioplastic-producing enzyme that catalyzes the production of a PHB bioplastic molecule from substrates present in the fiber-producing plant,
    wherein the coding sequence is selected from sequences encoding ketothiolase, acetoacetyl CoA reductase, and PHB synthase, wherein the promoter is operably connected upstream from the coding sequence; and (c) a transcriptional termination sequence operably connected to the coding sequence.

10. A genetic construct comprising:

(a) a fiber-specific promoter isolated from cotton plants; and (b) a coding sequence encoding ketothiolase, acetoacetyl CoA reductase, or PHB synthase wherein the promoter is operably connected upstream from the coding sequence; and (c) a transcriptional termination sequence operably connected to the coding sequence.

11. A cotton plant comprising in its genome heterologous genetic constructs encoding acetoacetyl CoA reductase and PHB synthase, wherein each construct comprises:

(a) a fiber-specific promoter isolated from cotton plants; and (b) a coding sequence encoding a bioplastic-producing enzyme that catalyzes the production of a PHB bioplastic molecule from substrates present in the fiber-producing plant wherein the coding sequence is selected from sequences encoding acetoacetyl CoA reductase and PHB synthase, wherein the promoter is operably connected upstream from the coding sequence; and (c) a transcriptional termination sequence operably connected to the coding sequence wherein the plant contains constructs encoding acetoacetyl CoA reductase and PHB synthase.

12. A cotton plant cell comprising in its genome heterologous genetic constructs encoding acetoacetyl CoA reductase and PHB synthase, wherein each construct comprises:

(a) a fiber-specific promoter isolated from cotton plants and (b) a coding sequence encoding a bioplastic-producing enzyme that catalyzes the production of a PHB bioplastic molecule from substrates present in the fiber-producing plant wherein the coding sequence is selected from sequences encoding acetoacetyl CoA reductase and PHB synthase, wherein the promoter is operably connected upstream from the coding sequence; and (c) a transcriptional termination sequence operably connected to the coding sequence, wherein the plant contains constructs encoding acetoacetyl CoA reductase and PHB synthase.

* * * * *